United States Patent [19]

Nakao et al.

[11] Patent Number: 4,716,158
[45] Date of Patent: Dec. 29, 1987

[54] 7-(2-AMINOTHIAZOL-4-YL)-2-(SYN)-METHOXYIMINOACETAMIDO)-3-METHOXYMETHYL-3-CEPHAM-4-CARBOXYLATES

[75] Inventors: Hideo Nakao; Koichi Fujimoto; Sadao Ishihara; Shinichi Sugawara; Isamu Igarashi, all of Tokyo, Japan

[73] Assignee: Sankyo Company Limited, Tokyo, Japan

[21] Appl. No.: 873,114

[22] Filed: Jun. 10, 1986

Related U.S. Application Data

[60] Continuation of Ser. No. 467,786, Feb. 18, 1983, abandoned, which is a division of Ser. No. 304,988, Sep. 23, 1981, Pat. No. 4,486,425.

[30] Foreign Application Priority Data

Sep. 30, 1980 [JP] Japan .................. 55-136449
Apr. 13, 1981 [JP] Japan .................. 56-55231
Jun. 10, 1981 [JP] Japan .................. 56-89116

[51] Int. Cl.$^4$ ................. C07D 501/34; A61K 31/545
[52] U.S. Cl. ...................... 514/202; 540/222
[58] Field of Search ..................... 540/222; 514/202

[56] References Cited

U.S. PATENT DOCUMENTS

| | | | |
|---|---|---|---|
| 3,935,204 | 1/1976 | Dahlen et al. ................ | 424/246 |
| 4,008,246 | 2/1977 | Ochiai et al. ................. | 544/28 |
| 4,024,137 | 5/1977 | Cook et al. ................... | 544/28 |
| 4,098,888 | 7/1978 | Ochiai et al. ................. | 544/28 |
| 4,380,541 | 4/1983 | Ochiai et al. ................. | 544/28 |
| 4,409,215 | 10/1983 | Takaya et al. ................ | 544/28 |

FOREIGN PATENT DOCUMENTS 29557 6/1981 European Pat. Off. .
034536 8/1981 European Pat. Off. .

OTHER PUBLICATIONS

Takahashi et al., "Alkanoylalkyl Cephalosporanates", Chem. Abst. 78:111337(v)(1973).
Takahashi et al., "Acyloxy Alkyl Cephalosporanates," Chem. Abst. 78:124612(f) and 124613(g)(1973).
Nakao et al., 7-Methoxycephalosporin Compounds Chem. Abst. 146752t (1979).
Walter E. Wright et al., "Orally Active Esters of Cephalosporin (pp. 1155-1160) Antibiotics, II Synthesis and biological Properties of the Acetoxymethyl Ester of Cefamandole", The Journal of Antibiotics, vol. XXXII, No. 11, Nov. 1979.
W. J. Wheeler et al., "Orally Active Esters of Cephalosporin Antibiotics . . . " Journal of Medicinal Chemistry, 1979, vol. 22, No. 6, pp. 657-661.

Primary Examiner—Nicholas S. Rizzo
Attorney, Agent, or Firm—Frishauf, Holtz, Goodman & Woodward

[57] ABSTRACT

Compounds of formula (I):

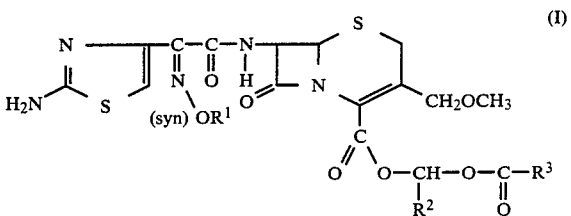

wherein:
R$^1$ represents a lower alkyl group selected from methyl groups and ethyl groups;
R$^2$ represents a hydrogen atom or a methyl group; and
R$^3$ represents a group selected from C$_1$—C$_5$ alkoxy groups,
and pharmaceutically acceptable acid addition salts thereof have valuable antibiotic activity and are suitable for oral administration. They may be prepared by a variety of synthetic routes.

5 Claims, No Drawings

7-(2-AMINOTHIAZOL-4-YL)-2-(SYN)-METHOXYIMINOACETAMIDO)-3-METHOXYMETHYL-3-CEPHAM-4-CARBOXYLATES

This application is a continuation of application Ser. No. 467,786, filed Feb. 18, 1983, now abandoned, which is a division of Ser. No. 304,988, filed Sept. 23, 1981, now U.S. Pat. No. 4,486,425.

The present invention relates to a series of new cephalosporin compounds which are particularly suitable for oral administration, to processes and intermediates for preparing these compounds and to compositions containing the compounds.

Although many cephalosporin derivatives which exhibit excellent antibacterial activity have been discovered, most of them are for parenteral administration. However, except where massive doses of an antibiotic are to be administered quickly, the preferred route of administration is oral, as oral preparations can be administered by the patient himself without the need for trained supervision or assistance. Unfortunately, of the many cephalosporin derivatives discovered, very few possess a combination of superior antibacterial activity, broad antibacterial spectrum against both gram-negative and gram-positive bacteria (especially against *Staphylococcus aureus*) and the ability to be absorbed efficiently through the digestive tract.

For example, cephalothin, cefazolin and cefmetazole are widely used for parenteral administration, particularly by injection. However, when these compounds are administered orally, only about 5% of the does administered is recovered in the urine, showing their poor absorption through the digestive tract and their unsuitability for oral administration. This is thought to be due to the strong dissociation of the carboxy group at the 4-position (i.e. the low pKa value) and the strong acidity.

Because of this, many efforts have been made to improve the absorption of cephalosporin derivatives through the digestive tract by esterifying the 4-carboxy group but almost all such efforts have failed to obtain cephalosporin derivatives which are well absorbed through the digestive tract and which are therefore useful for oral administration; as described hereafter, in the one instance where absorption through the digestive tract has been significantly improved, the resulting compound lacks the desired broad antibacterial spectrum.

For example, the Journal of Antibiotics, 32 No. 11, 1155 (1979) discloses that the absorption of cefamandol through the digestive tract is not improved by esterification to prepare the acetoxymethyl ester, since this ester is only sparingly soluble in water. Although absorption of the ester through the digestive tract can be improved to a limited extent by administration of the ester in solution in certain organic solvents (such as propylene glycol), this is not a particularly good solution to the problem.

The Journal of Medicinal Chemistry, 22, 657 (1979), on the other hand, reports that the absorption through the digestive tract of another ester of a cephalosporin which is readily soluble in water, is not significantly improved due to chemical instability of the ester.

Furthermore, it is known that, in general, lower alkyl and benzhydryl esters of cephalosporins possess, in themselves, almost no antibacterial activity and that they are not hydrolyzed in vivo (which might otherwise convert them to an active acid) and hence they are not of value for therapeutic use, although they may be useful as synthetic intermediates.

Of the various cephalosporin derivatives known, one known class has a 2-(2-aminothiazol-4-yl)-2-alkoxyiminoacetamido group at the 7-position and may be represented by the following formula:

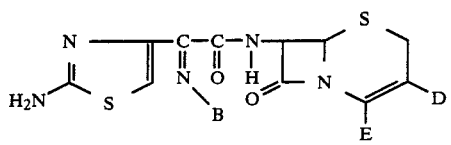

(in which B, D and E are substituents).

For example, Japanese Patent Application Kokai (i.e. as laid-open to public inspection) No. 149296/76 which corresponds to U.S. Pat. No. 4,098,888 discloses the following compounds:
 (a) 7-[2-(2-aminothiazol-4-yl)-2-methoxyiminoacetamido]-3-methyl-3-cephem-4-carboxylic acid;
 (b) 3-acetoxymethyl-7-[2-(2-aminothizaol-4-yl)-2-methoxyiminoacetamido]-3-cephem-4-carboxylic acid; and
 (c) 7-[2-(2-aminothiazol-4-yl)-2-methoxyiminoacetamido]-3-(1-methyl-1H-tetrazol-5-yl)thiomethyl-3-cephem-4-carboxylic acid.

We have discovered that the percentage recovery of these compounds in urine (which is a measure of their suitability for oral administration) is only 3.2%, 1.5% and 2%, for compounds (a), (b) and (c), respectively; these compounds are, accordingly, unsuitable for oral administration.

Likewise, Japanese Patent Application Kokai No. 86188/81 published July 13, 1981 which corresponds to European Patent Application No. 29,557 published June 3, 1981 (both published after the Sept. 30, 1980 filing date of the priority Japanese Application No. 136449/1980) disclose 7-[2-(2-aminothiazol-4-yl)-2-methoxyiminoacetamido]-3-methoxymethyl-3-cephem-4-carboxylic acid (d), which is the free carboxylic acid corresponding to certain of the compounds of the present invention. We have, however, found that the recovery rate in urine of compound (d) is only 5.5% and it is, therefore, unsuitable for oral administration. The Specification also discloses certain esters, particularly the t-butyl and benzhydryl esters, of cephalosporin compounds related to compound (d). However, as stated above, such esters are not believed to be readily convertible in vivo to the corresponding carboxylic acid and, as a result, may not be effective in actual use.

Japanese Patent Application Kokai No. 9296/79 which corresponds to U.S. Pat. No. 4,278,793 and 34795/78 which corresponds to U.S. Pat. No. 4,278,671 disclose the following pivaloyloxymethyl esters:
 (e) pivaloyloxymethyl 3-acetoxymethyl-7-[2-(2-aminothiazol-4-yl)-2-methoxyiminoacetamido]-3-cephem-4-carboxylate and
 (f) pivaloyloxymethyl 7-[2-(2-aminothiazol-4-yl)-2-methoxyiminoacetamido]-3-(1-methyl-1H-tetrazol-5-yl)thiomethyl-3-cephem-4-carboxylate.

We have also found that the recovery rate in urine of these compounds is only 8% and 14% for compounds (e) and (f), respectively, and these compounds also are unsuitable for oral administration.

Comparing the recovery rates of compounds (a), (b) and (c) with the recovery rates of compounds (e) and (f), the results are rather surprising, since it is known that the absorption of ampicillin through the digestive tract is considerably improved by converting it to the pivaloyloxymethyl ester.

The above-mentioned Japanese Patent Application Kokai No. 34795/78 also discloses pivaloyloxymethyl 7-[2-(2-aminothiazol-4-yl)-2-methoxyiminoacetamido]-3-methyl-3-cephem-4-carboxylate, hereinafter referred to as "compound (g)". We have carried out extensive studies of this compound and have found that is exhibits very good recovery in urine, at a level almost comparable with that of the compounds of the present invention, thus suggesting that it may well be suitable for oral administration. However, as will be shown hereafter, compound (g), when administered orally, is hydrolyzed and converted in vivo to the corresponding carboxylic acid which, in turn, has poor activity against *Staphylococcus aureus*. Failure to inhibit the growth of this bacterium, which is perhaps one of the most important from the clinical point of view, could be a disadvantage in actual use.

It is, accordingly, clear from the above discussion that preparation of a cephalosporin derivative which meets the triple requirements of good absorption through the digestive tract, high antibacterial activity and a broad antibacterial spectrum, is not a simple matter. The cephalosporin nucleus includes many points at which different substituents may be introduced and the introduction of a particular substituent to improve one property may adversely affect other properties in a quite unpredictable way. Moreover, it has clearly been demonstrated that, even where a particular chemical modification is known to improve the properties of one particular compound (e.g. as with the preparation of the pivaloyloxymethyl ester to improve the absorption of ampicillin), that is not any indication that a similar modification will similarly improve the properties of any other compound.

We have now surprisingly discovered a limited class of cephalosporin derivatives which can be administered orally as they are readily absorbed through the digestive tract and which are then readily hydrolyzed and converted in vivo to the corresponding carboxylic acid which, in turn, shows quite outstanding activity against both gram-positive and gram-negative bacteria.

Accordingly, the present invention consists in compounds of formula (I):

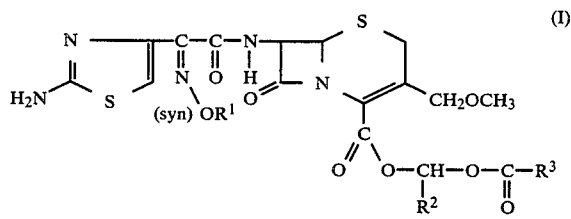

in which:

$R^1$ represents a methyl group o an ethyl group;

$R^2$ represents a hydrogen atom or a methyl group; and $R^3$ represents a $C_1$-$C_5$ alkyl or alkoxy group;

and pharmaceutically acceptable acid addition salts thereof.

The invention also provides a pharmaceutical composition comprising, as active ingredient, one or more of the compounds of the invention in admixture with a pharmaceutically acceptable carrier or diluent.

The invention also provides a variety of processes for preparing the compounds of the invention.

In the compounds of formula (I), when $R^3$ represents an alkyl group having from 1 to 5 carbon atoms, it is preferably a methyl, ethyl, propyl, isopropyl, butyl, isobutyl, sec-butyl, t-butyl, pentyl, isopentyl or t-pentyl group, most preferably a t-butyl group. $R^3$ most preferably represents a alkyl group having from 1 to 5 carbon atoms when $R^2$ represents a hydrogen atom.

When $R^3$ represents an alkoxy group having from 1 to 5 carbon atoms, it is preferably a methoxy, ethoxy, propoxy, isopropoxy, butoxy, isobutoxy, sec-butoxy, t-butoxy, pentyloxy or 1-ethylpropoxy group, most preferably an ethoxy group. $R^3$ most preferably represents an alkoxy group having from 1 to 5 carbon atoms when $R^2$ represents a methyl group.

Examples of compounds of the invention are given in the following list; the compounds are hereafter identified by the numbers assigned to them in the list.

1. Acetoxymethyl 7-[2-(2-aminothiazol-4-yl)-2-methoxyiminoacetamido]-3-methoxymethyl-3-cephem-4-carboxylate 2. Propionyloxymethyl 7-[2-(2-aminothizaol-4-yl)-2-methoxyiminoacetamido]-3-methoxymethyl-3-cephem-4-carboxylate 3. 1-Acetoxyethyl 7-[2-(2-aminothiazol-4-yl)-2-methoxyiminoacetamido]-3-methoxymethyl-3-cephem-4-carboxylate 4. Propionyloxymethyl 7-[2-(2-aminothiazol-4-yl)-2-ethoxyiminoacetamido]-3-methoxymethyl-3-cephem-4-carboxylate 5. Isopropionyloxymethyl 7-[2-(2-aminothiazol-4-yl)-2-methoxyiminoacetamido]-3-methoxymethyl-3-cephem-4-carboxylate 6. Butyryloxymethyl 7-[2-(2-aminothiazol-4-yl)-2-ethoxyiminoacetamido]-3-methoxymethyl-3-cephem-4-carboxylate 7. 1-Propionyloxyethyl 7-[2-(2-aminothiazol-4-yl)-2-ethoxyiminoacetamido]-3-methoxymethyl-3-cephem-4-carboxylate 8. Isobutyryloxymethyl 7-[2-(2-aminothiazol-4-yl)-2-methoxyiminoacetamido]-3-methoxymethyl-3-cephem-4-carboxylate 9. Pivaloyloxymethyl 7-[2-(2-aminothiazol-4-yl)-2-methoxyiminoacetamido]-3-methoxymethyl-3-cephem-4-carboxylate 10. Pivaloyloxymethyl 7-[2-(2-aminothiazol-4-yl)-2-ethoxyiminoacetamido]-3-methoxymethyl-3-cephem-4-carboxylate 11. Isovaleryloxymethyl 7-[2-(2-aminothiazol-4-yl)-2-methoxyiminoacetamido]-3-methoxymethyl-3-cephem-4-carboxylate 12. 1-Pivaloyloxyethyl 7-[2-(2-aminothiazol-4-yl)-2-ethoxyiminoacetamido]-3-methoxymethyl-3-cephem-4-carboxylate 13. Methoxycarbonyloxymethyl 7-[2-(2-aminothiazol-4-yl)-2-methoxyiminoacetamido]-3-methoxymethyl-3-cephem-4-carboxylate 14. 1-Methoxycarbonyloxyethyl 7-[2-(2-aminothiazol-4-yl)-2-ethoxyiminoacetamido]-3-methoxymethyl-3-cephem-4-carboxylate 15. Ethoxycarbonyloxymethyl 7-[2-(2-aminothiazol-4-yl)-2-methoxyiminoacetamido]-3-methoxymethyl-3-cephem-4-carboxylate 16. 1-Ethoxycarbonyloxyethyl 7-[2-(2-aminothiazol-4-yl)-2-methoxyiminoacetamido]-3-methoxymethyl-3-cephem-4-carboxylate 17. 1-Ethoxycarbonyloxyethyl 7-[2-(2-aminothiazol-4-yl)-2-ethoxyiminoacetamido]-3-methoxymethyl-3-cephem-4-carboxylate 18. Propoxycarbonyloxymethyl 7-[2-(2-aminothiazol-4-yl)-2-ethoxyiminoacetamido]-3-methoxymethyl-3-cephem-4-carboxylate 19. 1-Isopropoxycarbonyloxyethyl 7-[2-(2-aminothiazol-4-yl)-2-methoxyiminoacetamido]-3-methoxymethyl-3-cephem-4-carboxylate 20. 1-Butoxycarbonyloxyethyl 7-[2-(2-aminothiazol-4-yl)-2-ethoxyiminoacetamido]-3-methoxymethyl-3-cephem-4-carboxylate.

21. Isobutoxycarbonyloxymethyl 7-[2-(2-aminothiazol-4-yl)-2-methoxyiminoacetamido]-3-methoxymethyl-3-cephem-4-carboxylate 22. 1-sec-Butoxycarbonyloxyethyl 7-[2-(2-aminothiazol-4-yl)-2-methoxyiminoacetamido]-3-methoxymethyl-3-cephem-4-carboxylate 23. 1-(1-Ethylpropoxycarbonyloxy)ethyl 7-[2-(2-aminothiazol-4-yl)-2-methoxyiminoacetamido]-3-methoxymethyl-3-cephem-4-carboxylate 24. 1-(1-Ethylpropoxycarbonyloxy)ethyl 7-[2-(2-aminothiazol-4-yl)-2-ethoxyiminoacetamido]-3-methoxymethyl-3-cephem-4-carboxylate 25. 3,3,3-Trimethylpropionyloxymethyl 7-[2-(2-aminothiazol-4-yl)-2-methoxyiminoacetamido]-3-methoxymethyl-3-cephem-4-carboxylate.

Of the compounds listed above, Compounds No. 9, 10, 16 and 17 are most preferred.

As indicated in the formula, the compounds of formula (I) of the present invention are in the synform which has been found to have much stronger anti-bacterial activity than the corresponding anti-isomers.

The compounds of formula (I) will form acid addition salts with various acids and the invention thus also includes such salts with pharmaceutically acceptable acids, for example inorganic acids (such as hydrochloric acid, sulphuric acid or phosphoric acid) or organic acids (such as methanesulphonic acid, benzenesulphonic acid or malonic acid). Of the acid addition salts, the hydrochlorides are most preferred.

The compounds of the present invention may be prepared by a number of methods, for example those described below.

METHOD 1

Compounds of formula (I) can be prepared by reacting a compound of formula (II):

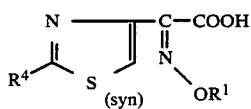   (II)

(in which $R^4$ represents an amino group or a protected amino group, and $R^1$ is as defined above) or a reactive derivative of said compound of formula (II) with a compound of formula (III):

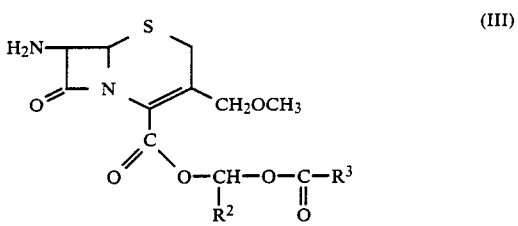   (III)

(in which $R^2$ and $R^3$ are as defined above) and, if necessary, deprotecting the group $R^4$.

In the above compounds of formula (II), preferred amino-protecting groups included in $R^4$ are those groups which may readily be removed to restore a free amino group, for example the trityl, formyl, t-butoxycarbonyl or 2-ethoxycarbonyl-1-methylvinyl groups, which may be removed by treatment with an acid, the 2,2,2-trichloroethoxycarbonyl group, which may be removed by reduction, the 2-methanesulphonylethoxycarbonyl group, which may be removed by treatment with an alkali, or the chloroacetyl group, which may be removed by treatment with thiourea.

The carboxylic acid of formula (II) may itself be used in the free form or it may be used in the form of a reactive derivative. Suitable reactive derivatives include the acid halide, the acid anhydride, mixed acid anhydrides, reactive esters, reactive amides and the acid azide. Preferred mixed acid anhydrides include mixed acid anhydrides with mono-(lower alkyl)carbonates, such as monomethyl carbonate or monoisobutyl carbonate, and mixed acid anhydrides with lower alkanoic acids, such as pivalic acid or trichloroacetic acid. Preferred reactive esters include the p-nitrophenyl ester, the pentachlorophenyl ester and the N-hydroxyphthalimide ester.

Where the compound of formula (II) is employed in the form of the free acid, we prefer to carry out the reaction in the presence of a condensing agent. Examples of suitable condensing agents include: di-substituted carbodiimides, such as dicyclohexylcarbodiimide; imidazolides, such as carbonyldiimidazole or thionyldiimidazole; N-ethoxycarbonyl-2-ethoxy-1,2-dihydroquinoline; or a Vilsmeier reagent prepared from dimethylformamide and, for example, phosphorus oxychloride or thionyl chloride.

Where a reactive derivative of the acid (II) is employed, the use of such a condensing agent is not necessary; however, for certain reactive derivatives, it may be desirable to carry out the reaction in the presence of a base. Examples of suitable bases include: alkali metal compounds, such as sodium bicarbonate, potassium bicarbonate, sodium carbonate or potassium carbonate; or aliphatic, aromatic or nitrogen-containing heterocyclic bases, such as triethylamine, N,N-dimethylaniline, N,N-diethylaniline, N-methylpiperidine, N-methylpyrrolidine, pyridine, collidine or lutidine.

The reaction of the acid (II) or its reactive derivative with the compound of formula (III) is preferably effected in the presence of a solvent, the nature of which is not critical, provided that it has no adverse effect upon the reaction. Preferred solvents include inert organic solvents (such as acetone, methyl ethyl ketone, tetrahydrofuran, dioxan, ethyl acetate, chloroform, methylene chloride, acetonitrile, dimethylformamide or dimethylsulphoxide) or a mixture of such a solvent and water.

There is no particular limitation on the reaction temperature, but we normally prefer to conduct the reaction at ambient temperature or with cooling. The time required for the reaction will vary, depending mainly upon the method of acylation and the reaction temperature, but usually the reaction will require a period which may vary from several tens of minutes to several tens of hours.

After completion of the reaction, the reaction product may be recovered from the reaction mixture by conventional means. For example, if a water-miscible solvent is employed, the solvent is preferably removed by distillation under reduced pressure and the residue is dissolved in a water-immiscible solvent. The resulting solution is then washed with an acid and a base and dried, after which the solvent is distilled off to give the desired product. If a water-immiscible solvent is employed for the reaction, the reaction mixture is washed with an acid or a base and dried, after which the solvent is distilled off. The product thus obtained may, if necessary, be further purified by conventional means, for example by chromatographic techniques.

The reaction required to remove the protecting group, if $R^4$ represents a protected imino group, is, as mentioned above, conventional and will vary depending upon the particular protecting group chosen. After removal of the protecting group, the desired product may be recovered from the reaction mixture and purified, e.g. as suggested above, to give the desired compound of formula (I).

METHOD 2

Compounds of formula (I) may be obtained by reacting a compound of formula (IV):

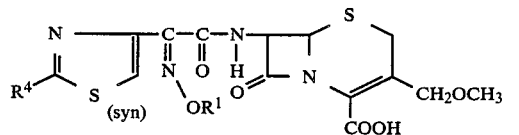

(IV)

(in which $R^1$ and $R^4$ are as defined above) or a reactive derivative thereof with a compound of formula (V):

(V)

(in which X represents a halogen atom, such as a chlorine, bromine or iodine atom, preferably an iodine atom, and $R^2$ and $R^3$ are as defined above) and then, if necessary, deprotecting the group represented by $R^4$.

Preferred reactive derivatives of the compound or formula (IV) are salts, for example salts with a metal (such as sodium or potassium) or with an organic amine (such as triethylamine). Where the free acid (IV) is employed, the reaction is preferably effected in the presence of an acid-binding agent, which may be organic or inorganic, for example potassium carbonate, sodium carbonate, sodium bicarbonate, triethylamine, dicyclohexylamine, pyridine or N,N-dimethylaniline.

The reaction is preferably effected in the presence of a solvent, the nature of which is not critical, provided that it has no adverse effect upon the reaction. Suitable solvents include dimethylformamide, dimethylacetamide, dimethyl sulphoxide, hexamethylphosphoric triamide or acetonitrile; a mixture of two or more such solvent may be employed, as may a mixture of one or more of these solvents with one or more other inert organic solvents. The reaction may be effected over a wide range of temperatures, but we generally prefer to conduct it at ambient temperature or with cooling. The time required for the reaction may vary from a period of several minutes to several hours.

After completion of the reaction, the reaction mixture is preferably diluted with a water-immiscible solvent, washed successively with an aqueous solution of potassium bisulphate and an aqueous basic solution and then dried, after which the solvent is distilled off to give the desired product. This product may be further purified by conventional means, for example by chromatographic techniques.

Where $R^4$ represents a protected amino group, it may be converted to a free amino group as described in Method 1.

METHOD 3

Compounds of formula (I) may be obtained by reacting a compound of formula (VI):

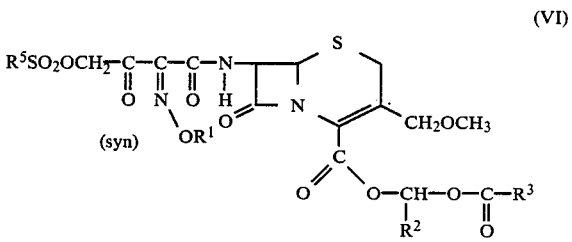

(VI)

(in which $R^5$ represents an alkyl group or an aryl group, and $R^1$, $R^2$ and $R^3$ are as defined above) with thiourea. Compounds of formula (VI) are new and themselves form part of the present invention.

In the compounds of formula (VI), when $R^5$ represents an alkyl group, it is preferably an alkyl group having from 1 to 6 carbon atoms, for example a methyl, ethyl, propyl, isopropyl, butyl, isobutyl, pentyl or hexyl group, more preferably a methyl or ethyl group. When $R^5$ represents an aryl group, it is preferably a substituted or unsubstituted phenyl or naphthyl group. In the case of substituted groups, there may be one or more substituents, normally from 1 to 5 substituents, and they may be the same or different. Suitable substituents include $C_1$-$C_4$ alkyl groups (e.g. methyl, ethyl, propyl, isopropyl or butyl), $C_1$-$C_4$ alkoxy groups (e.g. methoxy, ethoxy, propoxy, isopropoxy, butoxy or isobutoxy) and halogen atoms (e.g. chlorine, bromine or fluorine atoms). The most preferred aryl groups represented by $R^5$ are the phenyl and p-methylphenyl groups.

Representative examples of compounds of formula (VI) include:

26. Acetoxymethyl 7-(2-methoxyimino-3-oxo-4-p-toluenesulphonyloxybutyrylamino)-3-methoxymethyl-3-cephem-4-carboxylate 27. 1-Acetoxyethyl 7-(2-ethoxyimino-3-oxo-4-p-toluenesulphonyloxybutyrylamino)-3-methoxymethyl-3-cephem-4-carboxylate 28. Propionyloxymethyl 7-(4-benzenesulphonyloxy-2-methoxyimino-3-oxobutyrylamino)-3-methoxymethyl-3-cephem-4-carboxylate 29. 1-Propionyloxyethyl 7-(4-methanesulphonyloxy-2-methoxyimino-3-oxobutyrylamino)-3-methoxymethyl-3-cephem-4-carboxylate 30. 1-Butyryloxyethyl 7-(4-ethanesulphonyloxy-2-ethoxyimino-3-oxobutyrylamino)-3-methoxymethyl-3-cephem-4-carboxylate 31. Isobutyryloxymethyl 7-(2-methoxyimino-3-oxo-4-p-toluenesulphonyloxybutyrylamino)-3-methoxymethyl-3-cephem-4-carboxylate 32. Pivaloyloxymethyl 7-(2-methoxyimino-3-oxo-4-p-toluenesulphonyloxybutyrylamino)-3-methoxymethyl-3-cephem-4-carboxylate 33. Pivaloyloxymethyl 7-(2-ethoxyimino-3-oxo-4-p-toluenesulphonyloxybutyrylamino)-3-methoxymethyl-3-cephem-4-carboxylate 34. Pivaloyloxymethyl 7-(4-benzenesulphonyloxy-2-methoxyimino-3-oxobutyrylamino)-3-methoxymethyl-3-cephem-4-carboxylate 35. Pivaloyloxymethyl 7-(4-methanesulphonyloxy-2-methoxyimino-3-oxobutyrylamino)-3-methoxymethyl-3-cephem-4-carboxylate 36. Pivaloyloxymethyl 7-(4-ethanesulphonyloxy-2-ethoxyimino-3-oxobutyrylamino)-3-methoxymethyl-3-cephem-4-carboxylate 37. 1-Pivaloyloxyethyl 7-(2-methoxyimino-3-oxo-4-p-toluenesulphonyloxybutyrylamino)-3-methoxymethyl-3-cephem-4-carboxylate 38. Methoxycarbonyloxymethyl 7-(4-methanesulphonyl-oxy-2-methoxyimino-3-oxobutyrylamino)-3-methoxymethyl-3-cephem-4-carboxylate 39. Ethoxycarbonyloxymethyl 7-(4-benzenesulphonyloxy-2-ethoxyimino-3-oxobutyrylamino)-3-methoxymethyl-3-cephem-4-carboxylate 40. 1-Ethoxycarbonyloxyethyl 7-(2-methoxyimino-3-oxo-4-p-toluenesulphonyloxybutyrylamino)-3-methoxymethyl-3-cephem-4-carboxylate 41. 1-Ethoxycarbonyloxyethyl 7-(4-methanesulphonyloxy-2-methoxyimino-3-oxobutyrylamino)-3-methoxymethyl-3-cephem-4-carboxylate 42. 1-Ethoxycarbonyloxyethyl 7-(2-ethoxyimino-3-oxo-4-p-toluenesulphonyloxybutyrylamino)-3-methoxymethyl-3-cephem-4-carboxylate 43. Isopropoxycarbonyloxymethyl 7-(2-methoxyimino-3-oxo-4-p-toluenesulphonyloxybutyrylamino)-3-methoxymethyl-3-cephem-4-carboxylate.

44. 1-Butoxycarbonyloxyethyl 7-(4-benzenesulphonyloxy-2-methoxyimino-3-oxobutyrylamino)-3-methoxymethyl-3-cephem-4-carboxylate 45. 1-(1-Ethylpropoxycarbonyloxy)ethyl 7-(2-methoxyimino-3-oxo-4-p-toluenesulphonyloxybutyrylamino)-3-methoxymethyl-3-cephem-4-carboxylate 46. 3,3,3-Trimethylpropionyloxymethyl 7-(2-methoxyimino-3-oxo-4-p-toluenesulphonyloxybutyrylamino)-3-methoxymethyl-3-cephem-4-carboxylate Compounds of formula (VI) may be prepared, for example, by reacting a compound of formula (VII):

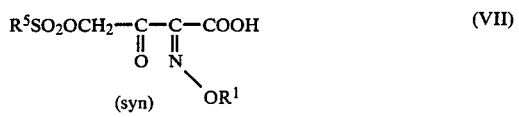

(in which $R^1$ and $R^5$ are as defined above) or a reactive derivative thereof with a compound of formula (III):

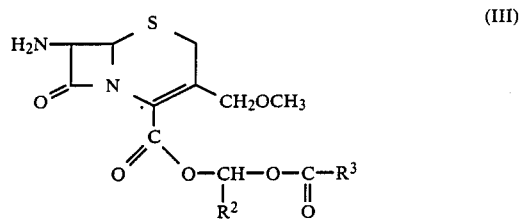

(in which $R^2$ and $R^3$ are as defined above). Compounds of formula (VII) are new and also part of the present invention. Representative examples of compounds of formula (VII) include:

47. 2-Methoxyimino-3-oxo-4-p-toluenesulphonyloxybutyric acid 48. 2-Ethoxyimino-3-oxo-4-p-toluenesulphonyloxybutyric acid 49. 4-Benzenesulphonyloxy-2-methoxyimino-3-oxobutyric acid 50. 4-Methanesulphonyloxy-2-methoxyimino-3-oxobutyric acid 51. 4-Ethanesulphonyloxy-2-ethoxyimino-3-oxobutyric acid.

Compounds of formula (VII) may, for example, be prepared by the series of reactions illustrated in the following reaction scheme for the preparation of the compound in which $R^5$ represents a p-tolyl group and $R^3$ represents a methyl group:

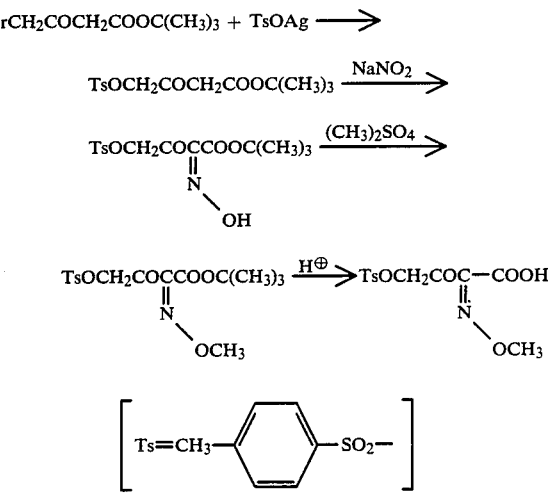

In the reaction to prepare the compound of formula (VI), the free acid of formula (VII) may be used as such or a reactive derivative of this free acid may be used. Where the free acid is used, the reaction is preferably carried out in the presence of a condensing agent, for example: a disubstituted carbodiimide, such as N,N'-dicyclohexylcarbodiimide; an azolide compound, such as N,N'-carbonylimidazole; a dehydrating agent, such as N-ethoxycarbonyl-2-ethoxy-1,2-dihydroquinoline, phosphorus oxychloride or an alkoxyacetylene; or a Vilsmeier reagent prepared from dimethylformamide and phosphorus oxychloride.

Where a reactive derivative of the acid of formula (VII) is employed, no such condensing agent is needed, but, depending upon the nature of the reactive derivative, the reaction may preferably be carried out in the presence of a base. Suitable bases include, for example: alkali metal compounds, such as sodium bicarbonate, potassium bicarbonate, sodium carbonate or potassium carbonate; and aliphatic, aromatic or nitrogen-containing heterocyclic bases, such as triethylamine, N,N-dimethylaniline, N,N-diethylaniline, N-methylpiperidine, N-methylpyrrolidine, pyridine, collidine or lutidine.

Preferred reactive derivatives of the acid (VII) include the acid halide, the acid anhydride, mixed acid anhydrides, active esters, active amides and the acid azide. Suitable mixed acid anhydrides include those with monoesters of carbonic acid (for example monomethyl carbonate or monoisobutyl carbonate) and those with lower alkanoic acids or lower haloalkanoic acids (such as pivalic acid or trichloroacetic acid). Suitable active esters include, for example, the p-nitrophenyl ester, the pentachlorophenyl ester, the N-hydroxyphthalimide ester and the N-hydroxybenzotriazole ester.

The reaction is preferably effected in the presence of a solvent, the nature of which is not critical, provided that it has no adverse effect upon the reaction. Suitable solvents include acetone, tetrahydrofuran, dioxan, ethyl acetate, chloroform, methylene chloride, dimethylformamide, acetonitrile and water, as well as mixtures of two or more of these solvents.

The reaction temperature is not particularly critical and the reaction is therefore normally performed at room temperature or with cooling. The time required for the reaction will vary, depending mainly on the nature of the acylating agent and on the reaction temperature, but the reaction will normally be complete within from 10 minutes to several tens of hours.

Upon completion of the reaction, the desired compound of formula (VI) may be recovered from the reaction mixture by conventional means and, although the compound may, if necessary, be purified (for example by recrystallization or by the various chromatographic techniques) it may also be used, without intermediate purification or separation, for the next step, that is to say the preparation of the desired compound of formula (I).

The reaction to produce the compound of formula (I) comprises contacting the compound of formula (VI) with thiourea, preferably in the presence of a suitable solvent. The nature of the solvent is not critical, provided that it has no adverse effect upon the reaction. Suitable solvents include water, methanol, ethanol, dimethylformamide, dimethylacetamide, acetonitrile, tetrahydrofuran and mixtures of two or more of these solvents.

If desired, a base (such as sodium acetate or sodium bicarbonate) may be added to the reaction mixture in order to promote the reaction or assist it to go to completion. Formation of by-products may be prevented by effecting the reaction in the presence of a buffer solution of pH 6.5–7.

The amount of thiourea employed is preferably 1 or more equivalents per equivalent of said compound of formula (VI).

The reaction temperature is not particularly critical and the reaction is therefore preferably effected at ambient temperature. The time required for the reaction will vary, depending upon the reaction conditions, but a period of from several tens of minutes to several hours will generally be required.

Upon completion of the reaction, the desired compound of formula (I) may be recovered by conventional means, for example by concentration under reduced pressure, extraction, reprecipitation or chromatography.

METHOD 4

Compounds of formula (I) may also be obtained by reacting a compound of formula (VIII):

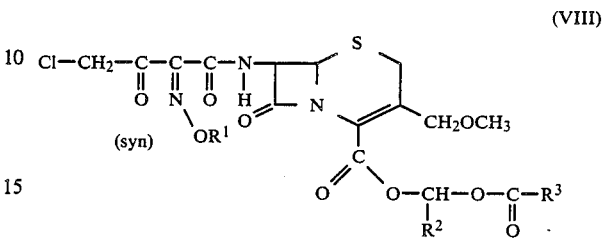

(in which $R^1$, $R^2$ and $R^3$ are as defined above) with thiourea.

Compounds of formula (VIII), which are new and also form part of the present invention, may be prepared by nitrosoating a compound of formula (IX):

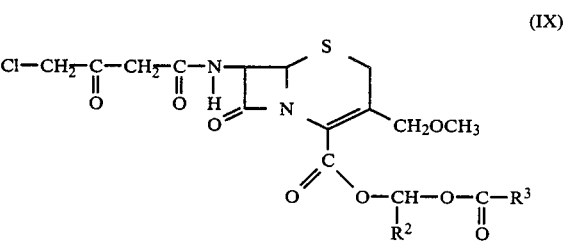

(in which $R^2$ and $R^3$ are as defined above) to give a compound of formula (X):

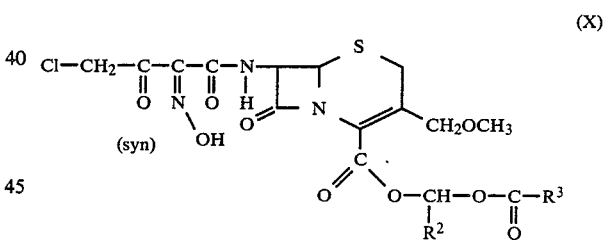

(in which $R^2$ and $R^3$ are as defined above) and then alkylating the hydroxy group attached to the imino nitrogen atom of said compound of formula (X).

Representative examples of the new compounds of formula (VIII) include:

52. Acetoxymethyl 7-(4-chloro-2-methoxyimino-3-oxobutyrylamino)-3-methoxymethyl-3-cephem-4-carboxylate 53. 1-Acetoxyethyl 7-(4-chloro-2-methoxyimino-3-oxobutyrylamino)-3-methoxymethyl-3-cephem-4-carboxylate 54. 1-Propionyloxymethyl 7-(4-chloro-2-methoxyimino-3-oxobutyrylamino)-3-methoxymethyl-3-cephem-4-carboxylate 55. 1-Ethoxycarbonyloxyethyl 7-(4-chloro-2-methoxyimino-3-oxobutyrylamino)-3-methoxymethyl-3-cephem-4-carboxylate 56. 1-Ethoxycarbonyloxyethyl 7-(4-chloro-2-ethoxyimino-3-oxobutyrylamino)-3-methoxymethyl-3-cephem-4-carboxylate 57. Methoxycarbonyloxymethyl 7-(4-chloro-2-methoxyimino-3-oxobutyrylamino)-3-methoxymethyl-3-cephem-4-carboxylate 58. Ethoxycarbonyloxymethyl 7-(4-chloro-2-ethoxyimino-3-oxobutyrylamino)-3-methoxymethyl-3-cephem-4-carboxylate 59. Isopropoxycarbonyloxymethyl 7-(4-chloro-2-methoxyimino-3-oxobutyrylamino)-3-methoxymethyl-3-cephem-4-carboxylate 60. Butoxycarbonyloxymethyl 7-(4-chloro-2-methoxyimino-3-oxobutyrylamino)-3-methoxymethyl-3-cephem-4-carboxylate 61. 1-Propionyloxyethyl 7-(4-chloro-2-methoxyimino-3-oxobutyrylamino)-3-methoxymethyl-3-cephem-4-carboxylate 62. 1-Butyryloxyethyl 7-(4-chloro-2-ethoxyimino-3-oxobutyrylamino)-3-methoxymethyl-3-cephem-4-carboxylate 63. Isovaleryloxymethyl 7-(4-chloro-2-methoxyimino-3-oxobutyrylamino)-3-methoxymethyl-3-cephem-4-carboxylate 64. Pivaloyloxymethyl 7-(4-chloro-2-methoxyimino-3-oxobutyrylamino)-3-methoxymethyl-3-cephem-4-carboxylate 65. Pivaloyloxymethyl 7-(4-chloro-2-ethoxyimino-3-oxobutyrylamino)-3-methoxymethyl-3-cephem-4-carboxylate 66. Isobutyryloxymethyl 7-(4-chloro-2-methoxyimino-3-oxobutyrylamino)-3-methoxymethyl-3-cephem-4-carboxylate 67. 1-Pivaloyloxyethyl 7-(4-chloro-2-methoxyimino-3-oxobutyrylamino)-3-methoxymethyl-3-cephem-4-carboxylate 68. 1-(1-Ethylpropoxycarbonyloxy)ethyl 7-(4-chloro-2-methoxyimino-3-oxobutyrylamino)-3-methoxymethyl-3-cephem-4-carboxylate 69. 3,3,3-Trimethylpropionyloxymethyl 7-(4-chloro-2-methoxyimino-3-oxobutyrylamino)-3-methoxymethyl-3-cephem-4-carboxylate.

The compound of formula (IX) can be prepared by acylating a compound of formula (III):

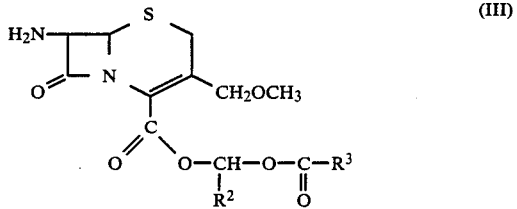

(in which $R^2$ and $R^3$ are as defined above) with 4-chloro-3-oxobutyryl chloride (which can be obtained by reacting diketene with chlorine). This acylation may be conducted by conventional means and is preferably effected in a solvent, the nature of which is not critical, provided that it has no adverse effect upon the reaction. Suitable solvents include methylene chloride, chloroform, tetrahydrofuran and dioxan. The acylation is preferably conducted in the presence of a base, preferably an organic base such as triethylamine, pyridine, N,N-dimethylaniline or N,N-diethylaniline. The reaction is preferably effected at about ambient temperature or at a lower temperature and will normally require a period of from several minutes to several hours. After completion of the reaction, the product of formula (IX) may be recovered and purified by conventional means, for example concentration, extraction with organic solvents, chromatographic techniques or recrystallization.

The nitrosoation of the compound of formula (IX) to prepare the compound of formula (X) may be effected by techniques known for the nitrosoation of reactive methylene groups. Such a nitrosoation reaction is normally effected using a metal salt of nitrous acid under acidic conditions or an ester of nitrous acid under suitable conditions. However, when preparing the compounds of the invention, it is necessary to carry out the reaction under such conditions that the cephalosporin ring system and the chlorine atom on the side chain at the 7-position do not participate in the reaction. It is, accordingly, desirable to carry out the reaction under weakly acidic or weakly basic conditions at a temperature below ambient. This reaction is normally carried out in the presence of a solvent, the nature of which is not critical, provided that it is capable of dissolving the compound of formula (IX) and does not have any adverse effect upon the reaction. Suitable solvents include formic acid, acetic acid, tetrahydrofuran, methanol, ethanol, chloroform, ethyl acetate and benzene, or a mixture of water with one or more of these solvents. The particular solvent chosen will depend upon the nature of the nitrosoating agent.

Examples of metal salts of nitrous acid employed as the nitrosoating agent include alkaline metal salts (such as sodium nitrite or potassium nitrite), preferably sodium nitrite. The nitrous acid ester is preferably an ester with a lower alcohol, for example pentyl nitrite or butyl nitrite.

Where a metal salt of nitrous acid is used as the nitrosoating agent, the reaction must be carried out under acidic conditions and, if an acidic solvent (such as formic acid or acetic acid) is not employed, the addition of an acid (which may be organic or inorganic) is necessary. Accordingly, we prefer to carry out the reaction using formic acid or acetic acid as the reaction solvent.

The reaction is preferably carried out at about ambient temperature or below and will require a period which may range from several minutes to several hours.

After completion of the reaction, the resulting product of formula (X) may be isolated and purified by conventional means, for example by concentration, extraction with organic solvents or chromatographic techniques.

The alkylation of the resulting compound of formula (X) to give the compound of formula (VIII) may be effected by reacting the compound of formula (X) with an alkylating agent, preferably in the presence of a solvent. The nature of the solvent is not critical, provided that it has no adverse effect upon the reaction. Suitable solvents include acetone, tetrahydrofuran, dioxan, methanol, ethanol, chloroform, ethyl acetate, diethyl ether and dimethylformamide, or a mixture of two or more of these solvents.

Suitable alkylating agents include dialkyl sulphates (e.g. dimethyl sulphate or diethyl sulphate), diazoalkanes (e.g. diazomethane) and alkyl halides (e.g. methyl iodide or ethyl iodide).

Except when a diazoalkane (such as diazomethane) is used as the alkylating agent, the reaction is preferably effected in the presence of a base. Suitable bases include: alkali metal carbonates, such as sodium carbonate or potassium carbonate; alkali metal hydroxides, such as sodium hydroxide or potassium hydroxide; and nitrogen-containing organic bases, such as triethylamine, pyridine or N,N-dimethylaniline.

The reaction is preferably effected at ambient temperature or below and will normally require a period of from several minutes to several hours. After completion of the reaction, the desired compound of formula (VIII) may be isolated and purified by conventional means, for example concentration, extraction with organic solvents, chromatographic techniques or recrystallization.

The reaction of the compound of formula (VIII) with thiourea to give the desired compound of formula (I) is essentially the synthesis of an aminothiazole derivative by reacting a haloketone with thiourea and may be carried out in much the same way as in common for this type of reaction.

The reaction is usually carried out in the presence of a solvent, the nature of which is not critical, provided that it has no adverse effect upon the reaction. The solvent is preferably an organic solvent (such as dimethylformamide, dimethylacetamide, methanol, ethanol or tetrahydrofuran) or a mixture of water with one or more of these organic solvents.

The thiourea is preferably employed in an amount of 1 or more equivalents per equivalent of said compound of formula (VIII).

In order to accelerate the reaction, sodium iodide may be added to the reaction mixture and the hydrogen chloride formed in the reaction may be neutralized by the addition of a neutral phosphate buffer solution.

The reaction is preferably effected at ambient temperature and will normally be complete within a period of from 1 to 10 hours.

When the reaction is complete, the desired compound of formula (I) may be isolated and purified by conventional means, for example by concentration, extraction with organic solvents, chromatographic techniques, reprecipitation or recrystallization.

EXAMPLE 5

Compounds of formula (I) may also be obtained by reacting a compound of formula (XI):

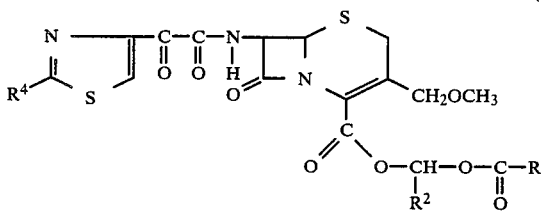

(XI)

(in which $R^2$, $R^3$ and $R^4$ are as defined above) with a compound of formula (XII):

$$H_2N-O-R^1 \quad (XII)$$

(in which $R^1$ is as defined above) and then, if necessary, deprotecting the group represented by $R^4$.

Compounds of formula (XI) are new and also form part of the present invention. They may be prepared by reacting a compound of formula (XIII):

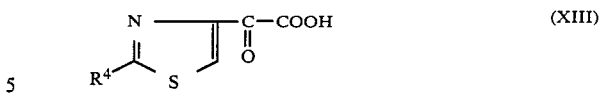

(XIII)

(in which $R^4$ is as defined above) or a reactive derivative thereof with a compound of formula (III).

Representative examples of the novel compounds of formula (XI) include:

70. Pivaloyloxymethyl 7-[2-(2-aminothiazol-4-yl)glyoxylamido]-3-methoxymethyl-3-cephem-4-carboxylate 71. Pivaloyloxymethyl 7-[2-(2-formamidothiazol-4-yl)glyoxylamido]-3-methoxymethyl-3-cephem-4-carboxylate 72. 1-Ethoxycarbonyloxyethyl 7-[2-(2-aminothiazol-4-yl)glyoxylamido]-3-methoxymethyl-3-cephem-4-carboxylate 73. 1-Ethoxycarbonyloxyethyl 7-[2-(2-formamidothiazol-4-yl)glyoxylamido]-3-methoxymethyl-3-cephem-4-carboxylate.

In the reaction to produce the compound of formula (XI), the compound of formula (XIII) may be used either in the form of the free acid or in the form of a reactive derivative thereof. When the free acid is used, the reaction is preferably effected in the presence of a condensing agent, for example: a disubstituted carbodiimide, such as N,N'-dicyclohexylcarbodiimide; an imidazolide, such as N,N'-carbonylimidazole or thionyldiimidazole; N-ethoxycarbonyl-2-ethoxy-1,2-dihydroquinoline; or a Vilsmeier reagent prepared from dimethylformamide and phosphorus oxychloride or thionyl chloride.

On the other hand, where a reactive derivative of the acid (XIII) is employed, there is no need to use a condensing agent, but, depending upon the nature of the reactive derivative, it may be preferred to effect the reaction in the presence of a base. Suitable bases include: alkali metal compounds, such as sodium bicarbonate, potassium bicarbonate, sodium carbonate or potassium carbonate; and aliphatic, aromatic or nitrogen-containing heterocyclic bases, such as triethylamine, N,N-dimethylaniline, N-methylpiperidine, N-methylpyrrolidine, pyridine, collidine or lutidine.

Reactive derivatives of the acid (XIII) include the acid halides, the acid anhydride, mixed acid anhydrides, active esters, active amides and the acid azide. Examples of suitable mixed acid anhydrides include those with monoesters of carbonic acid (for example monomethyl carbonate or monoisobutyl carbonate) and those with lower alkanoic acids and lower haloalkanoic acids (such as pivalic acid or trichloroacetic acid). Suitable active esters include, for example, the p-nitrophenyl ester, the pentachlorophenyl ester, the N-hydroxyphthalimide ester and the N-hydroxybenzotriazole ester.

The reaction is preferably effected in the presence of a solvent, the nature of which is not critical, provided that it has no adverse effect upon the reaction. Suitable solvents include acetone, methyl ethyl ketone, tetrahydrofuran, dioxan, ethyl acetate, chloroform, methylene chloride, dimethylformamide, acetonitrile and dimethyl sulphoxide, and mixtures of these solvents with water.

There is no particular limitation on the reaction temperature and accordingly the reaction is preferably effected at ambient temperature or with cooling. The time required for the reaction will vary, depending mainly on the nature of the acylating method and on the reaction temperature, but it will normally require a period of from 10 minutes to several tens of hours.

After completion of the reaction, the compound of formula (XI) may be recovered from the reaction mixture by conventional means and it may, if desired then be purified by conventional techniques such as chromatography.

The reaction of the compounds of formulae (XI) and (XII) is normally performed in a solvent, the nature of which is not critical, provided that it has no adverse effect upon the reaction. Suitable solvents include dimethylformamide, dimethylacetamide, acetonitrile and various alcohols, as well as mixtures of these solvents with water.

The alkoxyamine of formula (XII) is preferably employed in the form of a salt with an inorganic acid (such as hydrochloric acid, nitric acid or sulphuric acid) or an organic acid (such as acetic acid or benzoic acid).

The reaction temperature is not critical, but we normally prefer to carry out the reaction at a temperature from ambient temperature to 60° C. The time required for the reaction may vary, depending upon the reaction conditions, but will generally be from 10 minutes to several hours.

After completion of the reaction, the desired compound of formula (I) may be recovered from the reaction mixture by conventional means, for example by adding water and a water-immiscible solvent (such as ethyl acetate) to the reaction mixture, separating the organic layer under slightly alkaline conditions from the aqueous layer and then removing the organic solvent by distillation from this organic layer to give the desired compound.

Where the group $R^4$ in the compound obtained by this process is a protected amino group, it may be deprotected using the techniques described in relation to Method 1.

The desired compound of formula (I) may, if necessary, be purified by conventional means such as recrystallization and/or chromatographic techniques.

The compounds of formula (I) and their acid addition salts may advantageously be employed in antibacterial compositions for oral administration. In order that a compound may be used for this purpose, it is essential, as mentioned above, that it should be well absorbed through the digestive tract after oral administration. Good absorption through the digestive tract is demonstrated by a good recovery of the compound or of degration products in the urine after oral administration.

The prior art compound (g) has a recovery rate in urine of 66.7%, which is very nearly comparable with the recovery rates of 75.9% and 78% of Compounds 5 and 6, which are representative of the compounds of the present invention. These figures are quite satisfactory for the purposes of oral administration.

However, in addition to this good absorption through the digestive tract, it is desirable that compounds such as the prior art compound (g) and the compounds of the invention should, after hydrolization in vivo, be very active against gram-positive and gram-negative bacteria. The compounds of the invention, as well as compound (g), are hydrolized in vivo to the corresponding carboxylic acids and hence it is the antibacterial activities of these carboxylic acids, rather than of the esters, which are important from the clinical point of view. The activities of the carboxylic acids corresponding to Compounds No. 5 and 6 and to compound (g) against various bacteria are shown in the following Table, in terms of their minimal inhibitory concentrations (μg/ml).

TABLE

| | Compound 5 | Compound 6 | Compound (g) |
|---|---|---|---|
| *Staphylococcus aureus* 209P | 0.4 | 0.2 | 12.5 |
| *Staphylococcus aureus* 56 | 0.8 | 0.4 | 25 |
| *Escherichia coli* NIHJ | 0.4 | 0.8 | 0.8 |
| *Escherichia coli* 609 | 0.4 | 0.8 | 0.8 |
| *Shigella flexneri* 2a | 0.8 | 0.4 | 0.8 |
| *Klebsiella pneumoniae* 806 | 0.1 | 0.2 | 0.2 |
| Klebsiella sp. 846 | 0.8 | 0.8 | 1.5 |
| *Proteus vulgaris* | 0.01 | 0.01 | <0.1 |
| *Salmonella enteritidis* G. | 0.2 | 0.4 | 0.4 |

It is clear from the above Table, that the compounds of the invention and the prior art compound are all highly active against gram-negative bacteria, when administered orally. However, whereas Compounds 5 and 6 are active against *Staphylococcus aureus*, which is representative of the gram-positive bacteria, compound (g) has a rather low activity against these bacteria.

The compounds of the invention are preferably administered orally, for example in the form of capsules, tablets, powders, syrups or suspensions. The dosage depends upon the age, symptoms and body weight of the patient and on the duration of treatment, but the dosage may normally range from 0.2 g to 5 g per day, preferably from 0.5 g to 3 g per day for adults; however, if necessary, larger doses may be employed.

In the pharmaceutical compositions of the present invention, any conventional pharmaceutically acceptable carrier or diluent may be employed in admixture with the active compound or compounds. As the composition is generally intended to be administered orally, it is desirably presented in a form readily absorbed through the stomach or intestines. Tablets or capsules are normally in unit dosage form and may contain binding agents (e.g. syrup, gum arabic, gelatin, sorbitol, gum tragacanth or polyvinylpyrrolidone), diluents (e.g. lactose, sugar, corn starch, calcium phosphate, sorbitol or glycine), lubricants, (e.g. magnesium stearate, talc, polyethylene glycol or silica), distintegrating agents (e.g. potato starch) or wetting agents (e.g. sodium lauryl sulphate) or any combination thereof. The tablets may, if desired, be coated, e.g. with an enteric coating, as is well-known in the art.

Liquid formulations may be aqueous or oily suspensions, syrups, elixirs or similar compositions. Alternatively, the composition may be a dried product which can then be redissolved in water or another suitable vehicle before administration. Such liquid formulations may contain conventional additives, such as suspending agents (e.g. sorbitol syrup, methylcellulose, glucose/sugar syrup, gelatin, hydroxyethylcellulose, carboxymethylcellulose, aluminium stearate gel or hydrogenated edible fatl, emulsifying agents (e.g. lecithin, monooleic acid sorbitol or gum arabic), non-aqueous vehicles (e.g. almond oil, fractionated coconut oil, oily esters, propylene glycol or ethyl alcohol) or any combination of two or more thereof.

When the composition of the invention is formulated in unit dosage form, it preferably contains from 50 to 500 mg of the compound or compounds of the invention per unit dose.

The preparation of the compounds of the present invention is further illustrated by the following Examples and the preparation of certain intermediates is illustrated by the following Preparations. The compounds of the invention are all in the syn configuration.

PREPARATION 1

Pivaloyloxymethyl 3-methoxymethyl-7-phenoxyacetamido-3-cephem-4-carboxylate 1 g of sodium 3-methoxymethyl-7-phenoxyacetamido-3-cephem-4-carboxylate was dissolved in 50 ml of dimethyl sulphoxide, and 975 mg of pivaloyloxymethyl bromide were added thereto, after which the mixture was stirred at room temperature for 15 minutes. The mixture was then diluted with 200 ml of ethyl acetate, washed in turn with 50 ml of a saturated aqueous solution of sodium bicarbonate and 50 ml of a saturated aqueous solution of potassium bisulphate, and then dried over anhydrous magnesium sulphate. After filtering off the drying agent, the filtrate was concentrated under reduced pressure and the resulting residue was chromatographed through 100 g of silica gel eluted with a 1:1 by volume mixture of hexane and ethyl acetate, to afford 750 mg of the desired pivaloyloxymethyl 3-methoxymethyl-7-phenoxyacetamido-3-cephem-4-carboxylate.

Nuclear Magnetic Resonance spectrum (CDCl$_3$) δ ppm: 1.25 (9H, singlet, t-butyl); 3.35 (3H, singlet, OCH$_3$); 3.54 (2H, singlet, 2-cephem H$_2$); 4.29 (2H, singlet, CH$_2$ of methoxymethyl); 4.58 (2H, singlet, CH$_2$ of phenoxyacetamido); 5.01 (1H, doublet, J=5 Hz, 6-cephem H); 5.6–6.1 (3H, multiplet, 7-cephem H and CH$_2$ of pivaloyloxymethyl); 6.7–7.6 (6H, multiplet, C$_6$H$_5$ and NH).

PREPARATION 2

Pivaloyloxymethyl 7-amino-3-methoxymethyl-3-cephem-4-carboxylate p-toluenesulfonate 488 mg of phosphorus pentachloride were dissolved in 5 ml of dry methylene chloride, and then 120 mg of phosphorus oxychloride were added to the solution. Whilst the mixture was being stirred at room temperature, 247 mg of pyridine were added. The mixture was then cooled to −10° C., and 769 mg of pivaloyloxymethyl 3-methoxymethyl-7-phenoxyacetamido-3-cephem-4-carboxylate were added thereto. The temperature of the mixture was then allowed to rise gradually to room temperature. After stirring the mixture for 2 hours, it was again cooled to 0° C., and then 1.5 ml of propanol were added and the mixture was again stirred for 30 minutes. A small amount of water was added to the mixture, which was then stirred for a further 15 minutes. The mixture was diluted with 50 ml of ethyl acetate and washed with a saturated aqueous solution of sodium bicarbonate. The ethyl acetate layer was separated and dried over anhydrous magnesium sulphate. The drying agent was filtered off and the filtrate was concentrated by evaporation under reduced pressure. Diisopropyl ether was added to the residue and the wall of the vessel was scraped. The resulting precipitates were collected by filtration and dried to give 443 mg of the desired pivalo-yloxymethyl 7-amino-3-methoxymethyl-3-cephem-4-carboxylate. This compound was dissolved in 5 ml of ethyl acetate, and then an equimolar amount of p-toluenesulfonic acid monohydrate in 5 ml of ethyl acetate was added to the solution. The resulting mixture was allowed to stand at ambient temperature for 3 hours, affording 523 mg of the title compound melting at 160°–170° C. (with decomposition, recrystallized from methylene chloride and ethyl acetate) in the form of needles.

Elemental Analysis: Calculated for C$_{15}$H$_{22}$N$_2$O$_6$S.C$_7$H$_8$O$_3$S: C, 49.80%; N, 5.70%; N, 5.28%; S, 12.08%. Found: C, 49.76%; H, 5.60%; N, 5.00%; S, 12.06%.

PREPARATION 3

Benzhydryl 7-[2-(2-chloroacetamidothiazol-4-yl)-2-methoxyiminoacetamido]-3-methoxymethyl-3-cephem-4-carboxylate To 0.057 ml of dimethylformamide were added 0.061 ml of phosphorus oxychloride, with ice-cooling and stirring. The mixture was then stirred at 40° C. for 1 hour and then twice subjected to azeotropic distillation with dry methylene chloride. 1 ml of ethyl acetate was added to the resulting mixture, which was then vigorously stirred at room temperature whilst 200 mg of 2-(2-chloroacetamidothiazol-4-yl)-2-methoxyiminoacetic acid were added. Stirring was continued for a further 30 minutes to give a mixture (a).

Meanwhile, 200 mg of benzhydryl 7-amino-3-methoxymethyl-3-cephem-4-carboxylate and 145 mg of N,N-diethylaniline were dissolved in 5 ml of methylene chloride, and the mixture was stirred at −5° C. to give a mixture (b).

Mixture (a) was then added dropwise to mixture (b) and the mixtures were stirred together for 15 minutes, after which the resulting reaction mixture was concentrated by evaporation under reduced pressure. 20 ml of ethyl acetate and 5 ml of water were then added to the residue and the ethyl acetate layer was separated. This layer was washed in turn with 5 ml of a saturated aqueous solution of sodium carbonate, 5 ml of a 5% w/v aqueous solution of hydrogen chloride and finally 5 ml of a saturated aqueous solution of sodium chloride, after which the solution was dried over anhydrous magnesium sulphate. The drying agent was filtered off and the filtrate was concentrated by evaporation under reduced pressure. The resulting residue was chromatographed through 30 g of silica gel (Kieselgel 60), eluted with a 3:2 by volume mixture of hexane and ethyl acetate, to give 213 mg of the desired benzhydryl 7-[2-(2-chloroacetamidothiazol-4-yl)-2-methoxyiminoacetamido]-3-methoxymethyl-3-cephem-4-carboxylate.

Nuclear Magnetic Resonance spectrum (CDCl$_3$) δ ppm: 3.19 (3H, singlet, OCH$_3$ of methoxymethyl); 3.51 (2H, singlet, 2-cephem H$_2$); 4.09 (3H, singlet, OCH$_3$ of methoxyimino): 4.20 (2H, singlet, CH$_2$ of methoxymethyl); 4.22 (2H, singlet, CH$_2$ of chloroacetamido); 5.02 (1H, doublet, J=5 Hz, 6-cephem H); 5.86 (1H, doubled doublet, J=5 and 9 Hz, 7-cephem H); 6.7–7.6 (12H, multiplet).

PREPARATION 4

7-[2-(2-Aminothiazol-4-yl)-2-methoxyiminoacetamido]-3-methoxymethyl-3-cephem-4-carboxylic acid trifluoroacetate 200 mg of benzhydryl 7-[2-(2-chloroacetamidothiazol-4-yl)-2-methoxyiminoacetamido]-3-methoxymethyl-3-cephem-4-carboxylate, followed by 45 mg of thiourea, were dissolved in 5 ml of dimethylacetamide. The solution was maintained at room temperature for 2 hours. after which a saturated aqueous solution of sodium bicarbonate was added. The reaction mixture was then extracted with 20 ml of ethyl acetate and the extract was washed with water to remove excess thiourea and then dried over anhydrous magnesium sulphate. After the drying agent had been filtered off, the filtrate was concentrated by evaporation under reduced pressure. The resulting residue was chromatographed through 30 g of silica gel (Wacogel C-100), eluted with ethyl acetate, to afford 63 mg of benzhydryl 7-[2-(2-aminothiazol-4-yl)-2-methoxyiminoacetamido]-3-methoxymethyl-3-cephem-4-carboxylate.

The whole of this product was dissolved in 2 ml of anisole, and then 1 ml of trifluoroacetic acid was added to the solution, with ice-cooling and stirring. The mixture was then maintained at room temperature for 30 minutes, after which it was concentrated by evaporation under reduced pressure and diisopropyl ether was added to the residue. The resulting precipitates were collected by filtration and dried, to afford 27 mg of 7-[2-(2-aminothiazol-4-yl)-2-methoxyiminoacetamido]-3-methoxymethyl-3-cephem-4-carboxylic acid trifluoroacetate.

Nuclear Magnetic Resonance spectrum (deuteroacetone/$D_2O$) δ ppm:
3.29 (3H, singlet, $OCH_3$ of methoxymethyl); 3.57 (2H, singlet, 2-cephem $H_2$), 3.96 (3H, singlet, $OCH_3$ of methoxyimino); 4.27 (2H, singlet, $CH_2$ of methoxymethyl); 5.15 (1H, doublet, J=5.0 Hz, 6-cephem H); 5.97 (1H, doublet, J=5.0 Hz, 7-cephem H); 6.59 (1H, singlet).

PREPARATION 5

7-[2-(2-Chloroacetamidothiazol-4-yl)-2-methoxyiminoacetamido]-3-methoxymethyl-3-cephem-4-carboxylic acid A mixture of 7.65 g of benzhydryl 7-[2-(2-chloroacetamidothiazol-4-yl]-2-methoxyiminoacetamido]-3-methoxymethyl-3-cephem-4-carboxylate, 25 ml of methylene chloride, 5 ml of anisole and 20 ml of trichloroacetic acid was allowed to react at room temperature for 30 minutes. At the end of this time, 300 ml of diisopropyl ether were added to the reaction mixture and the resulting precipitates were collected by filtration, giving 5.95 g of 7-[2-(2-chloroacetamidothiazol-4-yl)-2-methoxyiminoacetamido]-3-methoxymethyl-3-cephem-4-carboxylic acid.

Nuclear Magnetic Resonance spectrum (deuteroacetone/deuterodimethyl sulphoxide) δ ppm:
3.30 (3H, singlet, $OCH_3$ of methoxymethyl); 3.60 (2H, singlet, 2-cephem $H_2$); 3.97 (3H, singlet, $OCH_3$ of methoxyimino); 4.25 (2 H, singlet, $CH_2$ of methoxymethyl); 4.37 (2H, singlet, $CH_2$ of chloroacetamido); 5.20 (1H, doublet, 6-cephem H); 5.90 (1H, doubled doublet, J=5.0 and 9.0 Hz, 7-cephem H); 7.40 (1H, singlet, 5-thiazole H); 9.50 (1H, doublet, J=9 Hz, 7-cephem NH).

PREPARATION 6

7-[2-(2-Aminothiazol-4-yl)-2-ethoxyiminoacetamido]-3-methoxymethyl-3-cephem-4-carboxylic acid trifluoroacetate Following the method of Preparation 3, 225 mg of 2-(2-chloroacetamidothiazol-4-yl)-2-ethoxyiminoacetic acid and 200 mg of benzhydryl 7-amino-3-methoxymethyl-3-cephem-4-carboxylate were reacted to give 280 mg of benzhydryl 7-[2-(2-chloroacetamidothiazol-4-yl)-2-ethoxyiminoacetamido]-3-methoxymethyl-3-cephem-4-carboxylate, in the form of a yellow powder.

Nuclear Magnetic Resonance spectrum ($CDCl_3$) δ ppm: 1.28 (3H, triplet, $OCH_2\underline{CH_3}$); 3.17 (3H, singlet, $OCH_3$); 3.50 (2H, broad singlet, 2-cephem $H_2$); 4.07 (2H, singlet, $CH_2$ of methoxymethyl); 4.0-4.5 (4H, multiplet, $O\underline{CH_2}CH_3$ and $CH_2$ of chloroacetamido); 5.07 (1H, doublet, J=5 Hz, 6-cephem H); 5.93 (1H, doubled doublet, J=5 and 9 Hz, 7-cephem H); 6.90 (1H, singlet, 5-thiazole H); 7.06 (1H, singlet, CH of benzhydryl); 7.31 [10H, singlet, $(C_6H_5)_2$]; 8.10 (1H, doublet, J=9 Hz, 7-cephem NH).

191 mg of this benzhydryl 7-[2-(2-chloroacetamidothiazol-4-yl)-2-ethoxyiminoacetamido]-3-methoxymethyl-3-cephem-4-carboxylate were then treated with 40 mg of thiourea, as described in Preparation 4, to give 117 mg of benzhydryl 7-[2-(2-aminothiazol-4-yl)-2-ethoxyiminoacetamido]-3-methoxymethyl-3-cephem-4-carboxylate, in the form of a pale pink powder, which was then treated with 1.5 ml of trifluoroacetic acid in a mixture of anisole and methylene chloride. When diisopropyl ether was added to the mixture, a precipitate was obtained and this was collected by filtration, to give 90 mg of 7-[2-(2-aminothiazol-4-yl)-2-ethoxyiminoacetamido]-3-methoxymethyl-3-cephem-4-carboxylic acid trifluoroacetate.

Nuclear Magnetic Resonance spectrum (deuterodimethyl sulphoxide) δ ppm: 1.27 (3H, triplet, J=7 Hz, $OCH_2\underline{CH_3}$); 3.23 (3H, singlet, $OCH_3$); 3.53 (2H, singlet, 2-cephem $H_2$); 4.16 (2H, quartet, J=7 Hz, $O\underline{CH_2}CH_3$); 4.20 (2H, singlet, $CH_2$ of methoxymethyl); 5.15 (1H, doublet, J=5 Hz, 6-cephem H); 5.78 (1H, doubled doublet, J=5 and 9 Hz, 7-cephem H); 6.80 (1H, singlet, 5-thiazole H); 9.70 (1H, doublet, J=9 Hz, 7-cephem NH); 8.5–10.0 (4H, broad multiplet, $NH_2$ and two COOH).

PREPARATION 7 t-Butyl 3-oxo-4-p-toluenesulphonyloxybutyrate

To 50 ml of dry acetonitrile were added 7.1 g of t-butyl 4-bromo-3-oxobutyrate and 9.45 g of silver p-toluenesulphonate, and the mixture was stirred for 3 days at room temperature, whilst shielding it from the light. The reaction mixture was then filtered and the filtrate was concentrated by evaporation in vacuo.

The resulting crystals containing an oily substance were dissolved in ethyl acetate and the insolubles were removed by filtration. The filtrate was concentrated by evaporation in vacuo, to give a brown, oily substance, which was purified by column chromatography through silica gel, eluted with a 4:1 by volume mixture of cyclohexane and ethyl acetate. The resulting colourless, oily substance was recrystillized from a 1:2 by volume mixture of diethyl ether and hexane, to afford 4.5 g of t-butyl 3-oxo-4-p-toluenesulphonyloxybutyrate, in the form of colourless prisms melting at 67°–69° C.

Nuclear Magnetic Resonance spectrum ($CDCl_3$) δ ppm: 1.43 (9H, singlet, t-butyl); 2.43 (3H, singlet, $CH_3$ of toluene); 3.43 (2H, singlet, —$CH_2COO$—); 4.60 (2H, singlet, —$SO_2OCH_2$—); 7.20–7.90 (4H, $C_6H_4$).

Elemental Analysis: Calculated for $C_{15}H_{20}O_6S$: C, 54.92%; H, 6.15%; S, 9.78%. Found: C, 55.03%, H, 6.07%; S, 9.86%.

PREPARATION 8 t-Butyl 2-hydroxyimino-3-oxo-4-p-toluenesulphonyloxybutyrate 4.5 g of t-butyl 3-oxo-4-p-toluenesulphonyloxybutyrate were dissolved in 40 ml of acetic acid, and then 1.42 g of sodium nitrite were added, at room temperature, to the solution over a period of 10 minutes. The mixture was then stirred at room temperature for 50 minutes, after which 200 ml of ethyl acetate were added and the mixture was then washed with an aqueous solution of sodium chloride. The ethyl acetate solution was dried over magnesium sulphate and, after filtering off the drying agent, the filtrate was concentrated by evaporation under reduced pressure to give a brown, oily substance. This oily substance was purified by column chromatography through silica gel, eluted with a 4:1 by volume mixture of cyclohexane and ethyl acetate, affording 1.66 g of t-butyl 2-hydroxyimino-3-oxo-4-p-toluenesulphonyloxybutyrate, in the form of colourless crystals, melting at 106°–108° C. (with decomposition, recrystallized from a 1:1 by volume mixture of diethyl ether and petroleum ether).

Nuclear Magnetic Resonance spectrum (CDCl$_3$) δ ppm: 1.52 (9H, singlet, t-butyl); 2.43 (3H, singlet, CH$_3$ of toluene); 5.04 (2H, singlet, —SO$_2$OCH$_2$CO—); 7.20–7.92 (4H, C$_6$H$_4$); 10.23 (1H, singlet, OH of hydroxyimino).

Elemental Analysis: Calculated for C$_{15}$H$_{19}$NO$_7$S: C, 50.48%; H, 5.36%; N, 3.92%; S, 8.98%. Found: C, 50.62%; H, 5.08%; N, 3.83%; S, 8.97%.

PREPARATION 9 t-Butyl 2-methoxyimino-3-oxo-4-p-toluenesulphonyloxybutyrate

To an ice-cooled solution of 1.66 g of t-butyl 2-hydroxyimino-3-oxo-4-p-toluenesulphonyloxybutyrate in 20 ml of dry acetone were added 960 mg of anhydrous potassium carbonate and 0.466 ml of dimethyl sulphate, and then the mixture was stirred at room temperature for 3 hours. The mixture was then poured into ice-water and extracted with methylene chloride. The extract was washed with an aqueous solution of sodium chloride, dried over magnesium sulphate and concentrated by evaporation under reduced pressure to give a brown, oily substance. This was purified by column chromatography through silica gel, eluted with a 4:1 by volume mixture of cyclohexane and ethyl acetate, to afford 650 mg of t-butyl 2-(syn)-methoxyimino-3-oxo-4-p-toluenesulphonyloxybutyrate, as a pale yellow oil.

Nuclear Magnetic Resonance spectrum (CDCl$_3$) δ ppm: 1.50 (9H, singlet, t-butyl); 2.43 (3H, singlet, CH$_3$ of toluene); 4.07 (3H, singlet, OCH$_3$); 5.05 (2H, singlet, —SO$_2$OCH$_2$CO—); 7.20–7.90 (4H, C$_6$H$_4$).

PREPARATION 10

2-Methoxyimino-3-oxo-4-p-toluenesulphonyloxybutyric acid

To a solution of 478 mg of t-butyl 2-(syn)-methoxyimino-3-oxo-4-p-toluenesulphonyloxybutyrate in 1 ml of methylene chloride were added 2 ml of trifluoroacetic acid, and the mixture was stirred at room temperature for 4 hours. The methylene chloride and the excess trifluoroacetic acid were then distilled off in vacuo, leaving a brown, oily substance, which was dissolved in diisopropyl ether and allowed to stand, affording 178 mg of 2-(syn)-methoxyimino-3-oxo-4-p-toluenesulphonyloxybutyric acid, in the form of colourless crystals melting at 131°–132° C. (with decomposition).

Elemental Analysis: Calculated for C$_{12}$H$_{13}$NO$_7$S: C, 45.72%; H, 3.84%; N, 4.45%; S, 10.18%. Found: C, 45.50%; H, 3.92%; N, 4.32%; S, 9.98%.

Nuclear Magnetic Resonance spectrum (deuteroacetone) δ ppm: 2.47 (3H, singlet, CH$_3$ of toluene); 4.10 (3H, singlet, OCH$_3$ ); 5.20 (2H, singlet, —SO$_2$OCH$_2$CO—); 7.25–7.95 (4H, C$_6$H$_4$); 9.80 (1H, broad singlet, COOH).

PREPARATION 11

Pivaloyloxymethyl 7-(2-methoxyimino-3-oxo-4-p-toluenesulphonyloxybutyrylamino)-3-methoxymethyl-3-cephem-4-carboxylate To a suspension of 464 mg of 2-(syn)-methoxyimino-3-oxo-4-p-toluenesulphonyloxybutyric acid in 20 ml of methylene chloride, cooled to −5° C., was added 0.204 ml of triethylamine, and the mixture was stirred for 5 minutes, until completely dissolved. To the resulting solution were added 0.17 ml of oxalyl chloride and a drop of dimethylformamide and the mixture was stirred at −5° C. for 20 minutes. On removing the solvent, there was left 2-(syn)-methoxyimino-3-oxo-4-p-toluenesulphonyloxybutyryl chloride. This was dissolved in 10 ml of methylene chloride, and then 0.394 ml of N,N-diethylaniline, followed by the methylene chloride solution, were added, at −5° C., to a solution of 530 mg of pivaloyloxymethyl 7-amino-3-methoxymethyl-3-cephem-4-carboxylate p-toluenesulphonate in 20 ml of methylene chloride. This mixture was stirred at −5° C. for 5 minutes, after which the solvent was distilled off. The resulting residue was dissolved in ethyl acetate and washed with dilute aqueous hydrochloric acid. The ethyl acetate layer was separated and dried over magnesium sulphate. After filtering off the drying agent, the filtrate was concentrated by evaporation under reduced pressure, to give a brown, oily substance. This was purified by column chromatography through silica gel eluted with a 4:1 by volume mixture of cyclohexane and ethyl acetate, to afford 510 mg of pivaloyloxymethyl 7-[2-(syn)-methoxyimino-3-oxo-4-p-toluenesulphonyloxybutyrylamino]-3-methoxymethyl-3-cephem-4-carboxylate, in the form of a colourless, foamy substance.

Nuclear Magnetic Resonance spectrum (CDCl$_3$) δ ppm: 1.22 (9H, singlet, t-butyl); 2.43 (3H, singlet, CH$_3$ of toluene); 3.30 (3H, singlet, OCH$_3$ of methoxymethyl); 3.51 (2H, singlet, 2-cephem H$_2$); 4.10 (3H, singlet, OCH$_3$ of methoxyimino); 4.27 (2H, singlet, CH$_2$ of methoxymethyl); 4.97 (1H, doublet, J=5.0 Hz, 6-cephem H); 5.07 (2H, singlet, —SO$_2$OCH$_2$CO—); 5.53–5.97 (3H, multiplet, 7-cephem H and —OCH$_2$— of pivaloyloxymethyl); 7.20–7.93 (5H, multiplet, 7-cephem NH and C$_6$H$_4$).

PREPARATION 12

Following the procedure described in Preparation 7, the following compounds were prepared:

t-Butyl 4-methanesulphonyloxy-3-oxobutyrate, as a pale yellow oil.

Nuclear Magnetic Resonance spectrum (CDCl$_3$) δ ppm: 1.47 (9H, singlet, t-butyl); 3.14 (3H, singlet, CH$_3$SO$_2$); 3.45 (2H, singlet, —COCH$_2$CO—); 4.87 (2H, singlet, —SO$_2$OCH$_2$CO—).

t-Butyl 4-ethanesulphonyloxy-3-oxobutyrate, a yellow oil.

Nuclear Magnetic Resonance spectrum (CDCl$_3$) δ ppm: 1.32–1.62 (9H+3H, singlet+triplet, t-butyl+CH$_3$CH$_2$SO$_2$); 3.30 (2H, quartet, J=7.0 Hz, CH$_3$CH$_2$SO$_2$); 3.47 (2H, singlet, —COCH$_2$CO—); 4.87 (2H, singlet, —SO$_2$OCH$_2$CO—).

t-Butyl 4-benzenesulphonyloxy-3-oxobutyrate, colourless needles melting at 94°–96° C.

Nuclear Magnetic Resonance spectrum (CDCl$_3$) δ ppm: 1.43 (9H, singlet, t-butyl); 3.43 (2H, singlet, —COCH$_2$CO—); 4.63 (2H, singlet, —SO$_2$OCH$_2$CO—); 7.40–8.03 (5H, multiplet, C$_6$H$_5$).

PREPARATION 13

Following the procedure described in Preparation 8, the following compounds were prepared:

t-Butyl 2-hydroxyimino-4-methanesulphonyloxy-3-oxobutyrate, white crystals melting at 103°–104° C. (with decomposition).

Nuclear Magnetic Resonance spectrum (CDCl$_3$/deuteroacetone) δ ppm: 1.57 (9H, singlet, t-butyl); 3.20 (3H, singlet, CH$_3$ of methanesulphonyl); 5.23 (2H, singlet, —SO$_2$OCH$_2$CO—); 11.93 (1H, singlet, OH of hydroxyimino).

t-Butyl 4-ethanesulphonyloxy-2-hydroxyimino-3-oxobutyrate, colourless crystals melting at 85°–87° C. (with decomposition).

Nuclear Magnetic Resonance spectrum (CDCl$_3$) δ ppm: 1.47 (3H, triplet, J=7.0 Hz, $\underline{CH_3}$CH$_2$SO$_2$); 1.57 (9H, singlet, t-butyl); 3.33 (2H, quartet, J=7.0 Hz, CH$_3$$\underline{CH_2}$SO$_2$); 5.23 (2H, singlet, —SO$_2$OCH$_2$CO—); 10.50 (1H, singlet, OH of hydroxyimino).

t-Butyl 4-benzenesulphonyloxy-2-hydroxyimino-3-oxobutyrate, colourless needles melting at 93°–95° C. (with decomposition).

Nuclear Magnetic Resonance spectrum (CDCl$_3$) δ ppm: 1.57 (9H, singlet, t-butyl); 5.07 (2H, singlet, —SO$_2$OCH$_2$CO—); 7.40–8.03 (5H, multiplet, C$_6$H$_5$); 10.17 (1H, broad singlet, OH of hydroxyimino).

PREPARATION 14

Following the procedures described in Preparation 9, the following compounds were prepared:

t-Butyl 4-methanesulphonyloxy-2-(syn)-methoxyimino-3-oxobutyrate, a colourless oil.

Nuclear Magnetic Resonance spectrum (CDCl$_3$) δ ppm: 1.54 (9H, singlet, t-butyl); 3.19 (3H, singlet, CH$_3$ of methanesulphonyl); 4.10 (3H, singlet, OCH$_3$ of methoxyimino); 5.23 (2H, singlet, —SO$_2$OCH$_2$CO—).

t-Butyl 4-ethanesulphonyloxy-2-(syn)-methoxyimino-3-oxobutyrate, a pale yellow oil.

Nuclear Magnetic Resonance spectrum (CDCl$_3$) δ ppm: 1.43 (3H, triplet, J=7.0 Hz, $\underline{CH_3}$CH$_2$SO$_2$); 1.50 (9H, singlet, t-butyl); 3.27 (2H, quartet, J=7.0 Hz, CH$_3$$\underline{CH_2}$SO$_2$); 4.07 (3H, singlet, OCH$_3$ of methoxyimino); 5.18 (2H, singlet, —SO$_2$OCH$_2$CO—).

t-Butyl 4-benzenesulphonyloxy-2-(syn)-methoxyimino-3-oxobutyrate, a colourless oil.

Nuclear Magnetic Resonance spectrum (CDCl$_3$) δ ppm: 1.50 (9H, singlet, t-butyl); 4.05 (3H, singlet, OCH$_3$ of methoxyimino); 5.07 (2H, singlet, —SO$_2$OCH$_2$CO—); 7.30–8.00 (5H, multiplet, C$_6$H$_5$).

PREPARATION 15

Following the procedure described in Preparation 10, the following compounds were prepared:

4-Methanesulphonyloxy-2-(syn)-methoxyimino-3-oxobutyric acid, a pale brown oil.

Nuclear Magnetic Resonator spectrum (deuteroacetone) δ ppm: 3.14 (3H, singlet, CH$_3$ of methanesulphonyl); 4.10 (3H, singlet, OCH$_3$ of methoxyimino); 5.27 (2H, singlet, —SO$_2$OCH$_2$CO—); 10.18 (1H, singlet, COOH).

4-Ethanesulphonyloxy-2-(syn)-methoxyimino-3-oxobutyric acid, melting at 85.5°–89° C.

Nuclear Magnetic Resonance spectrum (deuteroacetone) δ ppm: 1.40 (3H, triplet, J=7.0 Hz, $\underline{CH_3}$CH$_2$SO$_2$); 3.34 (2H, quartet, J=7.0 Hz, CH$_3$$\underline{CH_2}$SO$_2$); 4.13 (3H, singlet, OCH$_3$ of methoxyimino); 5.33 (2H, singlet, —SO$_2$OCH$_2$CO—); 11.10 (1H, broad singlet, COOH).

4-Benzenesulphonyloxy-2-(syn)-methoxyimino-3-oxobutyric acid, as crystals.

Nuclear Magnetic Resonance spectrum (deuteroacetone) δ ppm: 4.06 (3H, singlet, OCH$_3$ of methoxyimino); 5.17 (2H, singlet, —SO$_2$OCH$_2$CO—); 7.37–8.03 (5H, multiplet, C$_6$H$_5$); 10.33 (1H, singlet, COOH).

PREPARATION 16

Following the procedure described in Preparation 11, the following compounds were prepared:

Pivaloyloxymethyl 7-[4-methanesulphonyloxy-2-(syn)-methoxyimino-3-oxobutyrylamino]-3-methoxymethyl-3-cephem-4-carboxylate, a colourless, foamy substance.

Nuclear Magnetic Resonance spectrum (CDCl$_3$) δ ppm: 1.21 (9H, singlet, t-butyl); 3.16 (3H, singlet, CH$_3$ of methanesulphonyl); 3.30 (3H, singlet, OCH$_3$ of methoxymethyl); 3.53 (2H, broad singlet, 2-cephem H$_2$); 4.13 (3H, singlet, OCH$_3$ of methoxyimino); 4.24 (2H, singlet, CH$_2$ of methoxymethyl); 4.99 (1H, doublet, J=4.0 Hz, 6-cephem H); 5.23 (2H, singlet, —SO$_2$OCH$_2$CO—); 5.60–5.93 (3H, multiplet, 7-cephem H and CH$_2$ of pivaloyloxymethyl); 7.58 (1H, doublet, J=9.0 Hz, 7-cephem NH).

Pivaloyloxymethyl 7-[4-ethanesulphonyloxy-2-(syn)-methoxyimino-3-oxobutyrylamino]-3-methoxymethyl-3-cephem-4-carboxylate, a colourless, foamy substance.

Nuclear Magnetic Resonance spectrum (CDCl$_3$) δ ppm: 1.22 (9H, singlet, t-butyl); 1.43 (3H, triplet, J=7.0 Hz, $\underline{CH_3}$CH$_2$SO$_2$); 3.27 (2H, quartet, J=7.0 Hz, CH$_3$$\underline{CH_2}$SO$_2$); 3.30 (3H, singlet, OCH$_3$ of methoxymethyl); 3.54 (2H, broad singlet, 2-cephem H$_2$); 4.13 (3H, singlet, OCH$_3$ of methoxyimino); 4.26 (2H, singlet, CH$_2$ of methoxymethyl); 5.00 (1H, doublet, J=5.0 Hz, 6-cephem H); 5.27 (2H, singlet, —SO$_2$OCH$_2$CO—); 5.60–5.97 (3H, multiplet, 7-cephem H and CH$_2$ of pivaloyloxymethyl); 7.55 (1H, doublet, J=9.0 Hz, 7-cephem NH).

Pivaloyloxymethyl 7-[4-benzenesulphonyloxy-2-(syn)-methoxyimino-3-oxobutyrylamino]-3-methoxymethyl-3-cephem-4-carboxylate, a pale yellow, foamy substance.

Nuclear Magnetic Resonance spectrum (CDCl$_3$) δ ppm: 1.22 (9H, singlet, t-butyl); 3.30 (3H, singlet, OCH$_3$ of methoxymethyl); 3.52 (2H, broad singlet, 2-cephem H$_2$); 4.10 (3H, singlet, OCH$_3$ of methoxyimino); 4.27 (2H, singlet, CH$_2$ of methoxymethyl); 4.98 (1H, doublet, J=5.0 Hz, 6-cephem H); 5.08 (2H, singlet, —SO$_2$OCH$_2$CO—); 5.60–5.90 (3H, multiplet, 7-cephem H and CH$_2$ of pivaloyloxymethyl); 7.40–8.03 (6H, multiplet, C$_6$H$_5$, and 7-cephem NH).

PREPARATION 17

Pivaloyloxymethyl 7-(4-chloro-3-oxobutyrylamino)-3-methoxymethyl-3-cephem-4-carboxylate 725 mg of diketene were dissolved in 10 ml of dry methylene chloride and the solution stirred at −20° C. 30 ml of a carbon tetrachloride solution containing 620 mg of chlorine were then added dropwise to the solution, to produce 4-chloro-3-oxobutyryl chloride.

Meanwhile, 2 g of pivaloyloxymethyl 7-amino-3-methoxymethyl-3-cephem-4-carboxylate p-toluenesulphonate and 1.16 ml of N,N-diethylaniline were dissolved in 20 ml of methylene chloride. The resulting solution was cooled to −10° C., and then the 4-chloro-3-oxobutyryl chloride solution obtained as described above was added dropwise thereto. The mixture was then stirred at the same temperature for 30 minutes, after which it was concentrated by evaporation under reduced pressure. The resulting residue was dissolved in 50 ml of ethyl acetate and then washed in turn with water, a 5% w/v aqueous solution of hydrogen chloride and an aqueous solution of sodium chloride, after which it was dried over anhydrous magnesium sulphate and concentrated by evaporation under reduced pressure. The residue was dissolved in 3 ml of methylene chloride, and 30 ml of diethyl ether were added thereto, after which the mixture was allowed to stand. The resulting needle-like crystals were collected by filtration, washed with diethyl ether and dried to give 1.47 g of the title compound, melting at 131.5°–132.5° C.

Nuclear Magnetic Resonance spectrum (CDCl$_3$) δ ppm: 1.23 (9H, singlet, t-butyl); 3.31 (3H, singlet, OCH$_3$); 3.54 (2H, singlet, 2-cephem H$_2$); 3.65 (2H, singlet, CH$_2$); 4.26 (2H, singlet, CH$_2$); 4.29 (2H, singlet, CH$_2$); 4.97 (1H, doublet, J=5.5 Hz, 6-cephem H); 5.65–6.0 (3H, multiplet, 7-cephem H and CH$_2$ of pivaloyloxymethyl); 7.64 (1H, doublet, J=9 Hz, 7-cephem NH).

PREPARATION 18

Pivaloyloxymethyl 7-(4-chloro-2-hydroxyimino-3-oxobutyrylamino)-3-methoxymethyl-3-cephem-4-carboxylate 2.57 g of pivaloyloxymethyl 7-(4-chloro-3-oxobutyrylamino)-3-methoxymethyl-3-cephem-4-carboxylate were dissolved in 25 ml of acetic acid, and then 409 mg of sodium nitrite were added, little by little, at room temperature to the solution, after which the mixture was stirred for 30 minutes. The mixture was then diluted with 200 ml of ethyl acetate, washed three times with a saturated aqueous solution of sodium chloride, dried over anhydrous magnesium sulphate and then concentrated by evaporation under reduced pressure. The residue was twice subjected to azeotropic distillation using toluene and the resulting residue was dried, giving 2.7 g of the title compound as a foamy solid.

Nuclear Magnetic Resonance spectrum (CDCl$_3$) δ ppm: 1.23 (9H, singlet, t-butyl); 3.33 (3H, singlet, OCH$_3$ of methoxymethyl); 3.59 (2H, singlet, 2-cephem H$_2$); 4.33 (2H, singlet, CH$_2$ of methoxymethyl); 4.75 (2H, singlet, ClCH$_2$); 5.05 (1H, doublet, J=5.5 Hz, 6-cephem H); 5.6–6.1 (3H, multiplet, 7-cephem H and CH$_2$ of pivaloyloxymethyl); 9.3 (1H, doublet, J=9 Hz, 7-cephem NH).

PREPARATION 19

Pivaloyloxymethyl 7-[4-chloro-2-(syn)-methoxyimino-3-oxobutyrylamino]-3-methoxymethyl-3-cephem-4-carboxylate 5 g of pivaloyloxymethyl 7-(4-chloro-2-hydroxyimino-3-oxobutyrylamino)-3-methoxymethyl-3-cephem-4-carboxylate were dissolved in 40 ml of tetrahydrofuran. To the resulting solution was added a solution of 2 g of sodium carbonate in 40 ml of water, followed by 5 g of dimethyl sulphate, after which the mixture was stirred for 30 minutes. The mixture was then diluted with 150 ml of ethyl acetate, and washed twice with 60 ml each in turn of a saturated aqueous solution of sodium bicarbonate and a saturated aqueous solution of potassium bisulphate, after which it was dried over anhydrous magnesium sulphate and concentrated by evaporation under reduced pressure. The residue was chromatographed through 100 g of silica gel eluted with a 3:1 by volume mixture of chloroform and ethyl acetate, to give a solid containing the title compound. This solid was dissolved in 30 ml of diethyl ether and then left to stand under ice-cooling, to produce crystals, which were washed with diethyl ether and then dried, affording 1.9 g of the title compound as needles melting at 168.5°–169.5° C.

Nuclear Magnetic Resonance spectrum (CDCl$_3$) δ ppm: 1.24 (9H, singlet, t-butyl); 3.33 (3H, singlet, OCH$_3$ of methoxymethyl); 3.57 (2H, singlet, 2-cephem H$_2$); 4.19 (3H, singlet, OCH$_3$ of methoxyimino); 4.30 (2H, singlet, CH$_2$ of methoxymethyl); 4.60 (2H, singlet, ClCH$_2$); 5.03 (1H, doublet, J=5.5 Hz, 6-cephem H); 5.6–6.1 (3H, multiplet, 7-cephem H and CH$_2$ of pivaloyloxymethyl); 7.19 (1H, doublet, J=9 Hz NH).

PREPARATION 20

Pivaloyloxymethyl 7-[4-chloro-2-(syn)-ethoxyimino-3-oxobutyrylamino]-3-methoxymethyl-3-cephem-4-carboxylate The procedure described in Preparation 19 was repeated, but using diethyl sulphate in place of the dimethyl sulphate. The title compound was obtained in the form of needles melting at 171°–172° C.

Nuclear Magnetic Resonance spectrum (CDCl$_3$) δ ppm: 1.23 (9H, singlet, t-butyl); 1.39 (3H, triplet, J=7 Hz); 3.35 (3H, singlet, OCH$_3$); 3.57 (2H, singlet, 2-cephem H$_2$); 4.32 (2H, singlet, CH$_2$ of methoxymethyl); 4.43 (2H, quartet, J=7 Hz); 4.60 (2H, singlet, ClCH$_2$); 5.04 (1H, doublet, J=5.5 Hz, 6-cephem H); 5.6–6.1 [3H, multiplet, 7-cephem H and CH$_2$ of pivaloyloxy-methyl 7.17 (1H, doublet, J=9 Hz, 7-cephem NH).

PREPARATION 21

Pivaloyloxymethyl 7-[2-(2-formamidothiazol-4-yl)glyoxylamido]-3-methoxymethyl-3-cephem-4-carboxylate To 0.544 ml of N,N-dimethylformamide was added, with ice-cooling, 0.582 ml of phosphorus oxychloride, and the resulting mixture was stirred at 40°–45° C. for 1 hour. The low boiling point materials were removed by allowing the mixture to stand for 5 minutes in vacuo, after which 10 ml of ethyl acetate, 1.25 g of 2-(2-formamidothiazol-4-yl)glyoxylic acid and 3 ml of N,N-dimethylformamide were added, in turn, to the resulting residue at room temperature. The mixture was stirred for 40 minutes and then added to a solution of 2.9 g of pivaloyloxymethyl 7-amino-3-methoxymethyl-3-cephem-4-carboxylate p-toluenesulphonate and 2.9 ml of N,N-diethylaniline in 30 ml of methylene chloride at a temperature of −20° C. to −30° C. The mixture was then stirred at 0° C. for 30 minutes, after which it was diluted with chloroform, washed in turn, with an aqueous solution of potassium bisulphite and an aqueous solution of sodium bicarbonate, and then dried over anhydrous magnesium sulphate. The solvent was removed by distillation and the residue was purified by column chromatography through silica gel eluted with a 2:1 by volume mixture of ethyl acetate and chloroform, to give 1.9 g of the title compound in the form of an amorphous powder.

Nuclear Magnetic Resonance sepctrum (deuterodimethylsulphoxide) δ ppm: 1.22 (9H, singlet, t-butyl); 3.32 (3H, singlet, OCH$_3$); 3.57 (2H, broad singlet, 2-cephem H$_2$) 4.32 (2H, broad singlet, CH$_2$ of methoxymethyl); 5.07 (1H, singlet, 6-cephem H); 5.7–6.0 (3H, multiplet, —COOCH$_2$O— and 7-cephem H); 8.03 (1H, broad doublet, J=9 Hz, 7-cephem NH); 8.97 (1H, singlet); 9.05 (1H, broad singlet).

PREPARATION 22

1-Ethoxycarbonyloxyethyl 7-[2-(2-formamidothiazol-4-yl)glyoxylamido]-3-methoxymethyl-3-cephem-4-carboxylate The procedure described in Preparation 21 was repeated, but using 2.8 g of 1-ethoxycarbonyloxyethyl 7-amino-3-methoxymethyl-3-cephem-4-carboxylate p-toluenesulphonate and 1.25 g of 2-(2-formamidothiazol-4-yl)glyoxylic acid, to give 1.5 g of the title compound.

Nuclear Magnetic Resonance spectrum (CDCl$_3$) δ ppm: 1.31 (3H, triplet, J=7 Hz, OCH$_2$CH$_3$); 1.59 (3H, doublet, J=6 Hz, CH$_3$ of carbonyloxyethyl);
3.32 (3H, singlet, OCH$_3$ of methoxymethyl); 3.56 (2H, broad singlet, 2-cephem H); 4.22 (1H, quartet; J=7 Hz, OCH$_2$CH$_3$) 4.32 (2H, singlet, CH$_2$ of methoxymethyl); 5.03 (1H, doublet, J=5 Hz, 6-cephem H); 6.00 (1H, doubled doublet, J=5+9 Hz, 7-cephem H); 6.7–7.1 (1H, multiplet, CHCH$_3$); 7.38 (1H, singlet, 5-thiazole H); 8.01 (1H, doublet, J=9 Hz, 7-cephem H); 8.60 (1H, singlet, HCO); 9–12 (broad singlet (HCONH).

EXAMPLE 1

Pivaloyloxymethyl 7-[2-(2-aminothiazol-4-yl)-2-methoxyiminoacetamido]-3-methoxymethyl-3-cephem-4-carboxylate To 71 mg of dimethylformamide were added, with ice-cooling and stirring, 135 mg of phosphorus oxychloride. The mixture was stirred at 40° C. for 1 hour and then subjected twice to azeotropic distillation using dry methylene chloride. To the resulting mixture was added 1 ml of ethyl acetate, after which, 265 mg of 2-(2-chloroacetamidothiazol-4-yl]-2-methoxyiminoacetic acid were added, with vigorous stirring at room temperature, to the mixture and stirring was continued for 30 minutes.

Meanwhile, 121 mg of pivaloyloxymethyl 7-amino-3-methoxymethyl-3-cephem-4-carboxylate and 141 mg of N,N-diethylaniline were dissolved in 5 ml of methylene chloride and stirred at −5° C. The resulting mixture was added dropwise to the mixture containing 2-(2-chloroacetamidothiazol-4-yl]-2-methoxyiminoacetic acid prepared as described above. The reaction mixture was stirred for 15 minutes and then concentrated by evaporation under reduced pressure. To the residue were added 20 ml of ethyl acetate and 5 ml of water, and the ethyl acetate layer was separated, washed, in turn, with 5 ml of a saturated aqueous solution of sodium bicarbonate, 5 ml of a 5% w/v aqueous solution of hydrogen chloride and 5 ml of a saturated aqueous solution of sodium chloride, and finally dried over anhydrous magnesium sulphate. The drying agent was filtered off and the filtrate was concentrated by evaporation under reduced pressure. The resulting residue was subjected to column chromatography through 10 g of silica gel eluted with a 2:1 by volume mixture of ethyl acetate and hexane, to afford 55 mg of pivaloyloxymethyl 7-[2-(2-chloroacetamidothiazol-4-yl)-2-methoxyiminoacetamido]-3-methoxymethyl-3-cephem-4-carboxylate.

This product was dissolved in 1 ml of dimethylacetamide, and 13.5 mg of thiourea were added to the resulting solution, which was then stirred at room temperature for 2 hours. The reaction mixture was then diluted with 20 ml of ethyl acetate, washed with a saturated aqueous solution of sodium bicarbonate and dried over anhydrous magnesium sulphate. The drying agent was filtered off and the filtrate was concentrated by evaporation under reduced pressure. The residue was subjected to column chromatography through 5 g of silica gel eluted with a 3:1 by volume mixture of ethyl acetate and hexane, to afford 36 mg of the title compound.

Nuclear Magnetic Resonance spectrum (deutroacetone) δ ppm: 1.19 (9H, singlet, t-butyl); 3.23 (3H, singlet, OCH$_3$ of methoxymethyl); 3.52 (2H, singlet, 2-cephem H$_2$); 3.90 (3H, singlet, OCH$_3$ of methoxyimino); 4.18 (2H, singlet, CH$_2$ of methoxymethyl); 5.12 (1H, doublet, J=5 Hz, 6-cephem H); 5.8–6.1 (3H, multiplet, 7-cephem H and CH$_2$ of pivaloyloxymethyl); 6.78 (1H, singlet, 5-thiazole H); 6.6–7.1 (2H, broad singlet, NH$_2$); 8.01 (1H, doublet, J=9 Hz, 7-cephem NH).

EXAMPLE 2

Following the procedure described in Example 1, the following compounds were prepared:

Acetoxymethyl 7-[2-(2-aminothiazol-4-yl)-2-methoxyiminoacetamido]-3-methoxymethyl-3-cephem-4-carboxylate.

Nuclear Magnetic Resonance spectrum (deuteroacetone) δ ppm: 2.10 (3H, singlet, CH$_3$CO); 3.22 (3H, singlet, OCH$_3$ of methoxymethyl); 3.52 (2H, singlet, 2-cephem H$_2$); 3.92 (3H, singlet, OCH$_3$ of methoxyimino); 4.20 (2H, singlet, CH$_2$ of methoxymethyl); 5.11 (1H, doublet, J=5 Hz, 6-cephem H); 5.6–6.3 (3H, multiplet, CH$_2$ of acetoxymethyl and 7-cephem H); 6.76 (1H, singlet, 5-thiazole H); 6.6–7.1 (2H, broad singlet, NH$_2$); 8.03 (1H, doublet, J=9 Hz, 7-cephem NH).

Isovaleryloxymethyl 7-[2-(2-aminothiazol-4-yl)-2-methoxyiminoacetamido]-3-methoxymethyl-3-cephem-4-carboxylate Nuclear Magnetic Resonance spectrum (CDCl$_3$) δ ppm: 0.99 (6H, doublet, J=6.5 Hz, two CH$_3$ of isovaleryl); 1.3–2.1 (1H, multiplet, CH of isovaleryl); 2.2–2.5 (2H, multiplet, CH$_2$ of isovaleryl); 3.32 (3H, singlet, OCH$_3$ of methoxymethyl); 3.56 (2H, broad singlet, 2-cephem H$_2$); 3.98 (3H, singlet, OCH$_3$ of methoxyimino); 4.30 (2H, singlet, CH$_2$ of methoxymethyl); 5.06 (1H, doublet, J=5.0 Hz, 6-cephem H); 5.8 (2H, broad singlet, NH$_2$); 5.92 (2H, singlet, COOCH$_2$OCO); 6.08 (1H, doubled doublet, J=5.0 and 9.0 Hz, 7-cephem H); 6.70 (1H, singlet, 5-thiazole H); 8.20 (1H, doublet, J=9.0 Hz, 7-cephem NH).

Pivaloyloxymethyl 7-[2-(2-aminothiazol-4-yl)-2-ethoxyiminoacetamido]-3-methoxymethyl-3-cephem-4-carboxylate, having the properties described in Example 8.

EXAMPLE 3

Following the precedure described in Example 1, 1-ethoxycarbonyloxyethyl 7-[2-(2-aminothiazol-4-yl)-2-methoxyiminoacetamido]-3-methoxymethyl-3-cephem-4-carboxylate was prepared.

Nuclear Magnetic Resonance spectrum (CDCl$_3$) δ ppm: 1.32 1.30 (3H, triplet, OCH$_2$CH$_3$); 1.59 1.61 (3H, doublet, CH$_3$ of carbonyloxyethyl); 3.33 3.32 (3H, singlet, OCH$_3$ of methoxymethyl); 3.57 (2H, singlet, 2-cephem H$_2$); 4.03 (3H, singlet, OCH$_3$ of methoxyimino); 4.23 4.21 (2H, quartet, OCH$_2$CH$_3$); 4.34 4.30 (2H, singlet, CH$_2$ of methoxymethyl); 5.05 5.10 (1H, doublet, J=5 Hz, 6-cephem H); 5.59 [1H, doubled doublet J=5+9 Hz, 7-cephem H]; 5.73 [2H, broad singlet NH$_2$]; 6.73 6.70 [1H, singlet, 5-thiazole H]; 6.7–7.1 [1H, multiplet, CH of ethoxycarbonyloxyethyl]; 7.90 [1H, doublet, J=9 Hz, 7-cephem NH].

EXAMPLE 4

Pivaloyloxymethyl 7-[2-(2-aminothiazol-4-yl)-2-methoxyiminoacetamido]-3-methoxymethyl-3-cephem-4-carboxylate To 10 ml of dimethyl sulphoxide were added 1 g of 7-[2-(2-chloroacetamidothiazol-4-yl)-2-(syn)-methoxyiminoacetamido]-3-methoxymethyl-3-cephem-4-carboxylic acid, 380 mg of bromomethyl pivalate and 240 mg of potassium fluoride, after which the mixture was stirred at room temperature for 1 hour. The mixture was then diluted with 100 ml of ethyl acetate and washed successively with water, a 5% w/v aqueous solution of sodium bicarbonate, a 10% w/v aqueous solution of potassium bisulphate and a saturated aqueous solution of sodium chloride, after which it was dried over anhydrous magnesium sulphate. The solvent was then distilled off under reduced pressure and the resulting residue was subjected to column chromatography through silica gel eluted with a 1:1 by volume mixture of chloroform and ethyl acetate, to give 300 mg of pivaloyloxymethyl 7-[2-(2-chloroacetamidothiazol-4-yl)-2-(syn)-methoxyiminoacetamido]-3-methoxymethyl-3-cephem-4-carboxylate as a pale yellow powder.

This compound was dissolved, with 60 mg of thiourea, in 3 ml of dimethylacetamide, and the solution was stirred at room temperature for 4 hours. The mixture was then poured into 10 ml of a saturated aqueous solution of sodium bicarbonate and extracted with ethyl acetate. The extract was washed with, in turn, a 10% w/v aqueous solution of potassium bisulphate and a saturated aqueous solution of sodium chloride, after which it was dried over magnesium sulphate and concentrated by evaporation under reduced pressure. The residue was purified by column chromatography through silica gel eluted with a 3:1 by volume mixture of ethyl acetate and hexane to give 200 mg of the title compound. This compound was identified by nuclear magnetic resonance and found to be identical with the compound obtained in Example 1.

EXAMPLE 5

Isobutyryloxymethyl 7-[2-(2-aminothiazol-4-yl)-2-methoxyiminoacetamido]-3-methoxymethyl-3-cephem-4-4-carboxylate The procedure described in Example 4 was repeated, except that the bromomethyl pivalate was replaced by 360 mg of bromomethyl isobutyrate. There were obtained 180 mg of isobutyryloxymethyl 7-[2-(2-aminothiazol-4-yl)-2-(syn)-methoxyiminoacetamido]-3-methoxymethyl-3-cephem-4-carboxylate, as a slightly yellow powder.

Nuclear Magnetic Resonance spectrum (CDCl$_3$) δ ppm: 1.20 (6H, doublet, J=6.5 Hz, two CH$_3$ of isobutyryl); 2.66 (1H, septet, J=6.5 Hz, CH of isobutyryl); 3.21 (3H, singlet, OCH$_3$ of methoxymethyl); 3.40 (2H, AB quartet, 2-cephem H$_2$); 4.01 (3H, singlet, OCH$_3$ of methoxyimino); 4.16 (2H, singlet, CH$_2$ of methoxymethyl); 5.05 (1H, doublet, J=5 Hz, 6-cephem H); 5.6–6.2 (5H, multiplet, NH$_2$, CH$_2$ of carbonyloxymethyl and 7-cephem H); 6.65 (1H, singlet, 5-thiazole H); 8.06 (1H, doublet, J=9 Hz, 7-cephem NH).

EXAMPLE 6

Propionyloxymethyl 7-[2-(2-aminothiazol-4-yl)-2-methoxyiminoacetamido]-3-methoxymethyl-3-cephem-4-carboxylate The procedure described in Example 4 was repeated except that the bromomethyl pivalate, was replaced by 340 mg of bromomethyl propionate, to give 165 mg of the title compound as an almost colourless powder.

Nuclear Magnetic Resonance spectrum (CDCl$_3$) δ ppm: 1.17 (3H, triplet, J=6.5 Hz, CH$_2$CH$_3$); 2.41 (2H, quartet, J=6.5 Hz, CH$_2$CH$_3$); 3.20 (3H, singlet, CH$_3$ of methoxymethyl); 3.35 (2H, AB quartet, 2-cephem H$_2$); 4.02 (3H, singlet, OCH$_3$ of methoxyimino); 4.17 (2H, singlet, CH$_2$ of methoxymethyl); 5.09 (1H, doublet, J=5 Hz, 6-cephem H); 5.6–6.3 (5H, multiplet, NH$_2$, CH$_2$ of carbonyloxymethyl and 7-cephem H); 6.68 (1H, singlet, 5-thiazole H); 8.25 (1H, doublet, J=9 Hz, 7-cephem NH).

EXAMPLE 7

Pivaloyloxymethyl 7-[2-(2-aminothiazol-4-yl)-2-methoxyiminoacetamido]-3-methoxymethyl-3-cephem-4-carboxylate To a solution of 45 mg of sodium 7-[2-(2-aminothiazol-4-yl)-2-methoxyiminoacetamido]-3-methoxymethyl-3-cephem-4-carboxylate (prepared from the corresponding trifluoroacetate) in 1 ml of dimethylacetamide were added, at −15° C., 27 mg of iodomethyl pivalate and the mixture was allowed to react for 15 minutes. At the end of this time, 20 ml of ethyl acetate were added to the reaction mixture, and the mixture was washed, in turn, with water, an aqueous solution of potassium bisulphate and an aqueous solution of sodium bicarbonate. The organic phase was separated and concentrated by evaporation under reduced pressure, and the residue was subjected to column chromatography through silica gel eluted with a 3:1 by volume mixture of ethyl acetate and hexane, to give 49 mg of the title compound, whose properties were identical with those of the compound obtained in Example 1.

EXAMPLE 8

Pivaloyloxymethyl 7-[2-(2-aminothiazol-4-yl)-2-ethoxyiminoacetamido]-3-methoxymethyl-3-cephem-4-carboxylate The procedure described in Example 7 was repeated, except that sodium 7-[2-(2-aminothiazol-4-yl)-2-ethoxyiminoacetamido]—3-methoxymethyl-3-cephem-4-carboxylate and iodomethyl pivalate were used, to give the title compound.

Nuclear Magnetic Resonance spectrum (CDCl$_3$) δ ppm: 1.22 (9H, singlet, t-butyl); 1.31 (3H, triplet, OCH$_2$CH$_3$); 3.30 (3H, singlet, OCH$_3$ of methoxymethyl); 3.53 (2H, singlet, 2-cephem H$_2$); 4.28 (2H, quartet, OCH$_2$CH$_3$); 4.30 (2H, singlet, CH$_2$ of methoxymethyl); 5.01 (1H, doublet, J=5 Hz, 6-cephem H); 5.7–6.2 (5H, multiplet, 7-cephem H, NH$_2$ and CH$_2$ of carbonyloxymethyl); 6.76 (1H, singlet, 5-thiazole H); 7.70 (1H, doublet, 5=9 Hz, 7-cephem NH).

EXAMPLE 9

1-Ethoxycarbonyloxyethyl 7-[2-(2-aminothiazol-4-yl)-2-ethoxyiminoacetamido]-3-methoxymethyl-3-cephem-4-carboxylate To a solution of 500 mg of sodium 7-[2-(2-aminothiazol-4-yl)-2-ethoxyiminoacetamido]-3-methoxymethyl-3-cephem-4-carboxylate in 5 ml of N,N-dimethylacetamide were added, with ice-cooling, 395 mg of 1-iodoethyl ethylcarbonate, and then the mixture was stirred at room temperature for 30 minutes. At the end of this time, 50 ml of ethyl acetate were added to the reaction mixture, which was then washed with, in turn, 20 ml of water, 20 ml of a saturated aqueous solution of sodium bicarbonate and 20 ml of an aqueous solution of sodium chloride. The mixture was then dried over anhydrous magnesium sulphate and the solvent was removed by distillation under reduced pressure, giving a residue, which was chromatographed through 20 g silica gel eluted with ethyl acetate, to afford 460 mg of the title compound.

Nuclear Magnetic Resonance spectrum (COCl$_3$) δ ppm: 1.30 (3H, triplet, $CH_3CH_2$); 1.32 (3H, triplet, $CH_3CH_2$); 1.59 (3H, doublet, J=6.0 Hz, $CH_3$ of carabonyloxyethyl); 3.30 (3H, singlet, $OCH_3$ of methoxymethyl); 3.52 (2H, broad singlet, 2-cephem H$_2$); 4.22 (2H, quartet, $CH_3CH_2$); 4.27 (2H, quartet, $CH_3CH_2$); 4.30 (2H, singlet, $CH_2$ of methoxymethyl); 5.05 (1H, doublet, J=5.0 Hz, 6-cephem H); 5.8 (2H, broad singlet, NH$_2$); 6.00 (1H, doubled doublet, J 5.0+9.0 Hz, 7-cephem H); 6.75 (1H, singlet, 5-thiazole H); 6.7–7.1 (1H, multiplet, CH of carbonyloxyethyl); 7.8 (1H, doublet, J=9 Hz, 7-cephem NH).

EXAMPLE 10

Pivaloyloxymethyl 7-[2-(2-aminothiazol-4-yl)-2-methoxyiminoacetamido]-3-methoxymethyl-3-cephem-4-carboxylate To a solution of 510 mg of pivaloyloxymethyl 7-[2-(syn)-methoxyimino-3-oxo-4-p-toluenesulphonyloxybutyrylamino]-3-methoxymethyl-3-cephem-4-carboxylate in 5 ml of ethanol were added 76 mg of thiourea and 84 mg of sodium acetate. 3 ml of water were then added dropwise to the mixture, after which the whole mixture was stirred at room temperature for 3.5 hours. At the end of this time, the ethanol was removed by distillation and the residue was dissolved in ethyl acetate, washed with an aqueous solution of sodium chloride and dried over anhydrous magnesium sulphate. The ethyl acetate was distilled off, giving a pale brown, foamy substance, which was purified by column chromatography through silica gel eluted with a 2:1 by volume mixture of ethyl acetate and methylene chloride, affording 392 mg of the title compound, in the form of a colourless foamy substance having the same properties as the product of Example 1.

EXAMPLE 11

Propionyloxymethyl 7-[2-(2-aminothiazol-4-yl)-2-methoxyiminoacetamido]-3-methoxymethyl-3-cephem-4-carboxylate The procedure described in Example 10 was repeated, but using 490 mg of propionyloxymethyl 7-[2-(syn)-methoxyimino-3-oxo-4-p-toluenesulphonyloxybutyrylamino]-3-methoxymethyl-3-cephem-4-carboxylate, to give 370 mg of the title compound, having properties identical with those of the product of Example 6.

EXAMPLE 12

The procedure described in Example 10 was repeated except that the pivaloyloxymethyl 7-[2-(syn)-methoxyimino-3-oxo-4-p-toluenesulphonyloxybutyrylamino]-3-methoxymethyl-3-cephem-4-carboxylate was replaced by 1-ethoxycarbonyloxyethyl 7-[2-(syn)-methoxyimino-3-oxo-4-p-toluenesulphonyloxybutyrylamino]-3-methoxymethyl-3-cephem-4-carboxylate or isobutyryloxymethyl 7-[2-(syn)-methoxyimino-3-oxo-4-p-toluenesulphonyloxybutyrylamino]-3-methoxymethyl-3-cephem-4-carboxylate, to give 1-ethoxycarbonyloxyethyl 7-[2-(2-aminothiazol-4-yl)-2-methoxyiminoacetamido]-3-methoxymethyl-3-cephem-4-carboxylate (having properties idential with those of the product of Example 3) and isobutyryloxymethyl 7-[2-(2-aminothiazol-4-yl)-2-methoxyiminoacetamido]-3-methoxymethyl-3-cephem-4-carboxylate (having properties identical with those of the product of Example 5), respectively.

EXAMPLE 13

The procedure described in Example 10 was repeated, except that 465 mg of pivaloyloxymethyl 7-[4-methanesulphonyloxy-2-(syn)-methoxyimino-3-oxobutyrylamino]-3-methoxymethyl-3-cephem-4-carboxylate and 152 mg of thiourea were used, to give 390 mg of pivaloyloxymethyl 7-[2-(2-aminothiazol-4-yl)-2-methoxyiminoacetamido]-3-methoxymethyl-3-cephem-4-carboxylate, having properties identical with those of the product of Example 1.

The same compound was also obtained following the same procedure, but using, in separate experiments, pivaloyloxymethyl 7-[4-ethanesulphonyloxy-2-(syn)-methoxyimino-3-oxobutyrylamino]-3-methoxymethyl-3-cephem-4-carboxylate or pivaloyloxymethyl 7-[4-benzenesulphonyloxy-2-(syn)-methoxyimino-3-oxobutyrylamino]-3-methoxymethyl-3-cephem-4-carboxylate.

EXAMPLE 14

Pivaloyloxymethyl 7-[2-(2-aminothiazol-4-yl)-2-methoxyiminoacetamido]-3-methoxymethyl-3-cephem-4-carboxylate 47 mg of pivaloyloxymethyl 7-[4-chloro-2-(syn)-methoxyimino-3-oxobutyrylamino]-3-methoxymethyl-3-cephem-4-carboxylate were dissolved in 5 ml of dimethylacetamide and then 14 mg of thiourea were added to the solution, which was then stirred at room temperature for 4 hours. The reaction mixture was diluted with 50 ml of ethyl acetate, washed three times, each time with 15 ml of water, dried over anhydrous magnesium sulphate and then concentrated by evaporation under reduced pressure. The resulting residue was dissolved in 1 ml of chloroform, and 20 ml of diisopropyl ether were added to the resulting solution. The precipitate produced was collected by filtration and dried, to give 50 mg of the title compound as a colourless powder having properties identical with those of the product of Example 1.

EXAMPLE 15

Pivaloyloxymethyl 7-[2-(2-aminothiazol-4-yl)-2-ethoxyiminoacetamido]-3-methoxymethyl-3-cephem-4-carboxylate The procedure described in Example 14 was repeated, except that the pivaloyloxymethyl 7-[4-chloro-2-(syn)-methoxyimino-3-oxobutyrylamino]-3-methoxymethyl-3-cephem-4-carboxylate was replaced by pivaloyloxymethyl 7-[4-chloro-2-(syn)-ethoxyimino-3-oxobutyrylamino]-3-methoxymethyl-3-cephem-4-carboxylate, to give the title compound as a colourless powder having properties identical with those of the product of Example 8.

EXAMPLE 16

Pivaloyloxymethyl 7-[2-(2-aminothiazol-4-yl)-2-methoxyiminoacetamido]-3-methoxymethyl-3-cephem-4-carboxylate (a) A solution of 0.25 g of pivaloyloxymethyl 7-[2-(2-formamidothiazol-4-yl)glyoxylamido]-3-methoxymethyl-3-cephem-4-carboxylate and 65 mg of methoxyamine hydrochloride in 2 ml of dimethylacetamide was stirred at 40° C. for 140 minutes. At the end of this time, ethyl acetate was added to the reaction mixture, which was then washed with a saturated aqueous solution of sodium chloride and dried over anhydrous magnesium sulphate. The solvent was removed by distillation and the residue was subjected to column chromatography through silica gel, eluted with a 2:1 by volume mixture of ethyl acetate and chloroform, to give 0.2 g of crude pivaloyloxymethyl 7-[2-(2-formamidothiazol-4-yl)-2-(syn)-methoxyiminoacetamido]-3-methoxymethyl-3-cephem-4-carboxylate, which was further purified by recrystallization from 1 ml of ethyl acetate, to give 170 mg of crystals melting at 172° C. (with decomposition).

Nuclear Magnetic Resonance spectrum (deuterodimethyl sulphoxide) δ ppm: 1.18 (9H, singlet, t-butyl); 3.22 (3H, singlet, OCH$_3$ of methoxymethyl); 3.58 (2H, broad singlet, 2-cephem H$_2$); 3.88 (3H, singlet, OCH$_3$ of methoxyimino); 4.14 (2H, singlet, CH$_2$ of methoxymethyl); 5.19 (1H, doublet, J=5 Hz, 6-cephem H); 5.82 (3H, multiplet, CH$_2$ of pivaloyloxymethyl and 7-cephem H); 7.37 (1H, singlet, 5-thiazole H); 8.47 (1H, singlet, HCO); 9.66 (1H, doublet, J=9 Hz, 7-cephem NH); 12.58 (1H, broad singlet, NH of formamido).

(b) To a solution of 2.6 g of the pivaloyloxymethyl 7-[2-(2-formamidothiazol-4-yl)-2-(syn)-methoxyiminoacetamido]-3-methoxymethyl-3-cephem-4-carboxylate prepared as described above in 72 ml of methanol were added, with ice-cooling, 0.7 ml of concentrated hydrochloric acid, and the mixture was stirred at room temperature for 2.5 hours. The methanol was removed by distillation in vacuo, and then 20 ml each of ethyl acetate and water were added to the residue, after which the mixture was neutralized by the addition of a saturated aqueous solution of sodium bicarbonate. The organic layer was washed with a saturated aqueous solution of sodium chloride, dried and then concentrated by evaporation under reduced pressure. The residue was dissolved in 13 ml of chloroform and the solution was added dropwise, with stirring, to 100 ml of diisopropyl ether. The resulting precipitate was collected by filtration, to give 2.2 g of the title compound in the form of a colourless powder whose properties were identical with those of the product of Example 1.

EXAMPLE 17

Pivaloyloxymethyl 7-[2-(2-aminothiazol-4-yl)-2-ethoxyiminoacetamido]-3-methoxymethyl-3-cephem-4-carboxylate The procedure described in Example 16(a) was repeated except that the methoxyamine hydrochloride was replaced by 75 mg of ethoxyamine hydrochloride, to give 150 mg of pivaloyloxymethyl 7-[2-(syn)-ethoxyimino-2-(2-formamidothiazol-4-yl)acetamido]-3-methoxymethyl-3-cephem-4-carboxylate, in the form of crystals melting at 153° C.

Nuclear Magnetic Resonance spectrum (deuterodimethyl (sulphoxide) δ ppm: 1.18 (9H, singlet, t-butyl); 1.28 (3H, triplet, OCH$_2$CH$_3$); 3.21 (3H, singlet, OCH$_3$ of methoxymethyl); 3.58 (2H, broad singlet, 2-cephem H$_2$); 4.15 (2H, singlet, CH$_2$ of methoxymethyl); 4.19 (2H, quartet, OCH$_2$CH$_3$); 5.19 (1H, doublet, J=5 Hz, 6-cephem H); 5.71–5.95 (3H, multiplet, CH$_2$ of pivaloyloxymethyl and 7-cephem H); 7.38 (1H, singlet, 5-thiazole H); 8.48 (1H, singlet, HCO); 9.64 (1H, doublet, J=8 Hz, 7-cephem NH); 12.60 (1H, broad singlet, NH of formamido).

The procedure described in Example 16(b) was repeated, except that 9.65 g of pivaloyloxymethyl 7-[2-(syn)-ethoxyimino-2-(2-formamidothiazol-4-yl)acetamido]-3-methoxymethyl-3-cephem-4-carboxylate, 170 ml of methanol and 2 ml of concentrated hydrochloric acid were reacted at room temperature for 3 hours, to give 8.7 g of the title compound in the form of a colourless powder whose properties were identical to those of the product of Example 8.

EXAMPLE 18

1-Ethoxycarbonyloxyethyl 7-[2-(2-aminothiazol-4-yl)-2-methoxyiminoacetamido)-3-methoxymethyl-3-cephem-4-carboxylate A mixture of 180 mg of 1-ethoxycarbonyloxyethyl 7-[2-(2-formamidothiazol-4-yl)-2-(syn)-methoxyiminoacetamido]-3-methoxymethyl-3-cephem-4-carboxylate, 5 ml of methanol and 0.05 ml of concentrated hydrochloric acid were reacted as described in Example 16(b), to give 120 mg of the title compound, in the form of a pale yellow powder whose properties were identical with those of the product of Example 3.

EXAMPLE 19

Methoxycarbonyloxymethyl 7-[2-(2-aminothiazol-4-yl)-2-methoxyiminoacetamido]-3-methoxymethyl-3-cephem-4-carboxylate To a solution of 500 mg of sodium 7-[2-(2-aminothiazol-4-yl)-2-(syn)-methoxyiminoacetamido]-3-methoxymethyl-3-cephem-4-carboxylate in 5 ml of dimethylacetamide were added, with ice-cooling, 500 mg of iodomethyl methylcarbonate, and the mixture was stirred for 30 minutes. At the end of this time, the reaction mixture was diluted with 50 ml of ethyl acetate, washed, in turn, with a saturated aqueous solution of sodium bicarbonate and an aqueous solution of sodium chloride and dried over anhydrous magnesium sulphate. The magnesium sulphate was removed by filtration and the filtrate was concentrated by evaporation under reduced pressure. The residue was purified by column chromatography through silica gel, eluted with ethyl acetate, to give 433 mg of the title compound in the form of a foamy substance.

Nuclear Magnetic Resonance spectrum (CDCl$_3$) δ ppm: 3.31 (3H, singlet, OCH$_3$ of methoxymethyl); 3.56 (2H, broad singlet, 2-cephem H$_2$); 3.84 (3H, singlet, OCH$_3$ of methoxycarbonyl); 4.00 (3H, singlet, OCH$_3$ of methoxyimino); 4.31 (2H, singlet, CH$_2$ of methoxymethyl); 5.05 (1H, doublet, 6-cephem H); 5.5–6.3 (5H, multiplet, 7-cephem H, CH$_2$ of carbonyloxymethyl and NH$_2$); 6.68 (1H, singlet, 5-thiazole H); 8.10 (1H, doublet, J=9.0 Hz, 7-cephem NH).

EXAMPLE 20

Ethoxycarbonyloxymethyl 7-[2-(2-aminothiazol-4-yl)-2-methoxyiminoacetamido]-3-methoxymethyl-3-cephem-4-carboxylate To a solution of 861 mg of sodium 7-[2-(2-chloroacetamidothiazol-4-yl]-2-(syn)-methoxyiminoacetamido]-3-methoxymethyl-3-cephem-4-carboxylate in 8.6 ml of dimethylacetamide were added, at −10° C., 565 mg of iodomethyl ethylcarbonate and the mixture was stirred for 1 hour. At the end of this time, 100 ml of ethyl acetate were added to the reaction mixture, which was then washed, in turn, with water, a saturated aqueous solution of sodium bicarbonate and an aqueous solution of sodium chloride, and then dried over magnesium sulphate. The organic layer was concentrated by evaporation under reduced pressure and the residue was purified by column chromatography through silica gel eluted with a 2:1 by volume mixture of ethyl acetate and chloroform, to give 696 mg of ethoxycarbonyloxymethyl 7-[2-(2-chloroacetamido-thiazol-4-yl)-2-(syn)-methoxyiminoacetamido]-3-methoxymethyl-3-cephem-4-carboxylate.

The whole of this compound was dissolved in 6.4 ml of dimethylacetamide, and 800 mg of thiourea were added to the resulting solution, after which the mixture was stirred at room temperature overnight. The mixture was then diluted with 100 ml of ethyl acetate, washed three times with water and dried over anhydrous magnesium sulphate. The solvent was removed by distillation and the residue was subjected to column chromatography through silica gel eluted with ethyl acetate, to give 220 mg of the title compound in the form of a foamy substance.

Nuclear Magnetic Resonance spectrum (CDCl$_3$) δ ppm: 1.32 (3H, triplet, J=7 Hz, CH$_3$ of ethoxy); 3.32 (3H, singlet, OCH$_3$ of methoxymethyl); 3.53 (2H, broad singlet, 2-cephem H$_2$); 3.98 (3H, singlet, OCH$_3$ of methoxyimino); 4.23 (2H, quartet, J=7 Hz, OC$\underline{H}_2$CH$_3$); 4.31 (2H, singlet, CH$_2$ of methoxymethyl); 5.04 (1H, doublet, J=6 Hz, 6-cephem H); 5.6–6.3 (5H, multiplet, 7-cephem H, CH$_2$ of carbonyloxymethyl and NH$_2$); 6.63 (1H, singlet, 5-thiazole H); 8.13 (1H, doublet, J=9.0 Hz, 7-cephem NH),

EXAMPLE 21

Isovaleryloxymethyl 7-[2-(2-aminothiazol-4-yl)-2-methoxyiminoacetamido]-3-methoxymethyl-3-cephem-4-carboxylate The procedure described in Example 20 was repeated to prepare the title compound, having the same properties as the second compound of Example 2.

EXAMPLE 22

Capsules for oral administration

The following mixture was compounded and enscapulated by conventional means with a No. 2 capsule, to give an encapsulated formulation:

| | |
|---|---|
| Pivaloyloxymethyl 7-[2-(2-amino-thiazol-4-yl)-2-(syn)-methoxyimino-acetamido]-3-methoxymethyl-3-cephem-4-carboxylate | 250 mg |
| Talc | 5 mg |
| Magnesium stearate | 6.7 mg |
| Sodium laurylsulphate | 0.3 mg |
| Lactose | 28 mg |

We claim:

1. Compounds of the formula (I):

wherein:
R$^1$ is a methyl group,
R$^2$ is a hydrogen atom or a methyl group, and
R$^3$ is a C$_1$–C$_4$ alkyl group; and
pharmaceutically acceptable acid addition salts thereof.

2. The compounds of claim 1, wherein R$^2$ is a hydrogen atom and R$^3$ is a C$_1$–C$_4$ alkyl group.

3. The compounds of claim 1, in the form of the hydrochlorides.

4. A pharmaceutical composition for oral administration comprising an effective amount of an antibiotic in admixture with a pharmaceuticlaly acceptable carrier or diluent, said antibiotic comprising a compound of the formula (I):

wherein:
R$^1$ is a methyl group,
R$^2$ is a hydrogen atom or a methyl group, and
R$^3$ is a C$_1$–C$_4$ alkyl group; and
a pharmaceutically acceptable acid addition salt thereof.

5. The pharmaceutical composition of claim 4, wherein said compound is pivaloyloxymethyl 7-[2-(2-aminothiazol-4-yl)-2-(syn)-methoxyiminoacetamido]-3-methoxymethyl-3-cephem-4-carboxylate and pharmaceutically acceptable acid addition salts thereof.

* * * * *

UNITED STATES PATENT AND TRADEMARK OFFICE
CERTIFICATE OF CORRECTION

PATENT NO. : 4,716,158

DATED : December 29, 1987

INVENTOR(S) : Hideo Nakao, et al

It is certified that error appears in the above-identified patent and that said Letters Patent is hereby corrected as shown below:

The term of this patent subsequent to December 4, 2001 has been disclaimed.

Signed and Sealed this

First Day of March, 1988

Attest:

DONALD J. QUIGG

*Attesting Officer*          *Commissioner of Patents and Trademarks*